(12) United States Patent
Woehrmann et al.

(10) Patent No.: US 8,633,225 B2
(45) Date of Patent: Jan. 21, 2014

(54) PIPERIDINIUM COMPOUNDS AND COSMETIC COMPOSITIONS CONTAINING THEM

(75) Inventors: Michael Woehrmann, Hamburg (DE); Lara Terstegen, Hamburg (DE); Annette Martin, Hamburg (DE); Melanie Sulzberger, Hamburg (DE)

(73) Assignee: Beiersdorf AG, Hamburg (DE)

( * ) Notice: Subject to any disclaimer, the term of this patent is extended or adjusted under 35 U.S.C. 154(b) by 482 days.

(21) Appl. No.: 12/940,284

(22) Filed: Nov. 5, 2010

(65) Prior Publication Data

US 2011/0044923 A1 Feb. 24, 2011

Related U.S. Application Data

(62) Division of application No. 11/449,720, filed on Jun. 9, 2006, now Pat. No. 7,851,633.

(51) Int. Cl.
*A61K 31/445* (2006.01)
*A61K 8/55* (2006.01)

(52) U.S. Cl.
USPC .......................................... 514/327; 546/222

(58) Field of Classification Search
USPC .......................................... 514/327; 546/222
See application file for complete search history.

(56) References Cited

U.S. PATENT DOCUMENTS

| 2,987,517 | A | | 6/1961 | Martin et al. ................. 546/212 |
| 3,312,709 | A | | 4/1967 | MacMillan ....................... 546/91 |
| 3,802,862 | A | * | 4/1974 | Bidlack .......................... 504/178 |
| 4,022,787 | A | | 5/1977 | Soldati et al. ................. 546/222 |
| 4,720,494 | A | | 1/1988 | Felger et al. ..................... 424/65 |
| 6,338,841 | B1 | | 1/2002 | Mattai et al. ..................... 424/65 |
| 6,482,837 | B1 | | 11/2002 | Wood ............................. 514/315 |
| 6,645,476 | B1 | | 11/2003 | Morschhauser et al. ...... 424/70.1 |

FOREIGN PATENT DOCUMENTS

| DE | 10029462 | 1/2002 |
| GB | 788126 | 12/1957 |
| GB | 1032646 | 6/1966 |
| GB | 2031727 | 4/1980 |
| WO | 03/026585 | 4/2003 |

OTHER PUBLICATIONS

MacMillian et al. "The antiperspirant . . . " J. Investigative Dermotology v.43p. 363-378 (1964).*
McMillan et al. "The antiperspirant . . . " CA62:54408 (1965).*
J. Biel et al., "Central Stimulants. II. Cholinergic Blocking Agents", Journal of Organic Chemistry, vol. 26, No. 10, pp. 4096-4103 (1961).
S. Coan et al., "Parasympathetic Blocking Agents. III. Phenylglycolic Acid Esters of N-Alkyl-4-Piperidinol", Journal of the American Chemical Society, vol. 78, No. 15, pp. 3701-3703 (1956).
Feriani et al., "Cholinergic Agents Structurally Related to Furtrethonium. 2. Synthesis and Antimuscarinic Activity of a Series of N-[5-[1'-Substituted-acetoxy)methyl]-2-furfuryl]dialkylamines", Journal of Medicinal Chemistry, vol. 37, No. 25, pp. 4278-4287 (1994).
G. Moersch et al., "The Synthesis of α-Hydroxycarboxylic Acids by Aeration of Lithiated Carboxylic Acids in Tetrahydrofuran Solution", Synthesis: Communications, vol. 1971, No. 12, pp. 647-648 (1971).
Formanek K., Weiss W.: "Vergleichende pharmakologische Untersuchungen von tertiaeren und den entsprechenden quartaeren Spasmolytica vom Estertypus", Arzneimittel-Forschung, vol. 13, 1963, pp. 66-68.
Macmillan K. F. S. et al.: „The Antiperspirant Action of Topically Applied Anticholinergics, Journal of Investigative Dermatology, vol. 43, 1964, pp. 363-377.

* cited by examiner

*Primary Examiner* — Celia Chang
(74) *Attorney, Agent, or Firm* — Abel Law Group, LLP

(57) ABSTRACT

Cosmetic or dermatological compositions which comprise at least one piperidinium salt, preferably a 4-[(2-cyclopentyl-2-hydroxyphenylacetyl)oxy]-1,1-dimethyl-piperidinium salt, and the use thereof, particularly as antiperspirants. This Abstract is neither intended to define the invention disclosed in this specification nor intended to limit the scope of the invention in any way.

24 Claims, No Drawings

PIPERIDINIUM COMPOUNDS AND COSMETIC COMPOSITIONS CONTAINING THEM

CROSS-REFERENCE TO RELATED APPLICATIONS

The present application is a divisional of U.S. patent application Ser. No. 11/449,720, filed Jun. 9, 2006, the entire disclosure of which is expressly incorporated by reference herein.

BACKGROUND OF THE INVENTION

1. Field of the Invention

The present invention relates to piperidinium compounds and in particular their use in compositions for topical application, in particular antiperspirants. Preferred piperidinium compounds include 1,1-dimethyl-4-[2-cyclopentyl-2-hydroxyphenylacetyl)oxy]-piperidinium salts and 1,1-dimethyl-4-[3-methyl-2-phenylvaleryl)oxy]-piperidinium salts, in particular 1,1-dimethyl-4-[(2-cyclopentyl-2-hydroxyphenylacetyl)oxy]-piperidinium bromide. Their use in therapeutically active or cosmetic compositions is advantageous.

2. Discussion of Background Information

Various chemical compounds for treating bladder diseases are known from U.S. Pat. No. 6,482,837, the entire disclosure whereof is incorporated by reference herein. Substituted N-methyl-4-piperidinium compounds, inter alia, are disclosed therein, a plurality of molecular residues and combinations and variations of these residues being described. The compounds disclosed in U.S. Pat. No. 6,482,837 serve all medical purposes and in particular the treatment of bladder diseases.

Furthermore, from the literature are known 4-[cyclopentylhydroxyphenylacetyl)oxy]-1,1-dimethyl-piperidinium with CAS number 807285-21-8 and 4-hydroxy-1,1-dimethylpiperidinium iodide, α-cyclopentyl mandelate with CAS number 113569-69-0 and 1,1-dimethyl-4-[3-methyl-2-phenylvaleryl)oxy]-piperidinium bromide with CAS number 100337-30-2. However, further information regarding these compounds, in particular on their possible applications, are not found in the literature.

In humans two different sweat glands are responsible for the development of perspiration and perspiration odor, which are more or less pronounced, depending on the area of the body. The eccrine sweat glands secrete mainly salt and water and usually do not contribute to the formation of odor. The apocrine sweat glands are responsible for the odor, which secrete fatty acids, cholesterines and other compounds. These substances are decomposed by bacteria on the skin, the breakdown products producing the odor typical of perspiration.

In order to suppress perspiration odor over a longer period, the use of cosmetic preparations is essential. The conventional cosmetic deodorants are based on different mechanisms of action that can also be combined: on the one hand deodorizing agents are used that suppress the growth of the bacteria causing the perspiration odor. These antimicrobial (bacteriostatic) agents include, e.g., triclosan, chlorhexidine and naturally occurring compounds such as farnesol and phenoxyethanol.

On the other hand, antiperspirants are used which prevent the secretion of sweat by blocking the sweat gland ducts. In the large majority of antiperspirants, the formation of perspiration is reduced by the use of so-called astringents—primarily aluminum salts such as aluminum hydroxychloride (aluminum chlorohydrate) or aluminum/zirconium salts.

Also the combination of astringents with antimicrobially active substances in one and the same composition is customary. Furthermore, fragrances are used to mask the perspiration odor.

However, the aluminum chlorohydrate conventionally used as an antiperspirant has various disadvantages due to the acid character and the active mechanism, which range from the known yellowish textile staining to perfume instabilities to a limited selection of formulas. It is a particular drawback for the user that residues can stain clothing in an unpleasant way and the low pH value (very acidic) of the cosmetic preparation negatively impacts the biological balance of the skin.

It would be desirable to provide compounds that are toxicologically harmless, can be easily incorporated without complications into therapeutically active or cosmetic preparations, are easy to synthesize and moreover have one or more additional advantageous properties. It would be particularly advantageous to provide substances for use in therapeutic or cosmetic compositions that have the effect of reducing or inhibiting perspiration.

It would also be desirable to provide effective cosmetics and in particular antiperspirant products that do not exhibit the disadvantages of the prior art and preferably render superfluous the necessity of the use of antiperspirant agents based on aluminum compounds or at least help to reduce them.

SUMMARY OF THE INVENTION

The present invention provides cosmetic or dermatological compositions which comprise at least one piperidinium salt of formula (I):

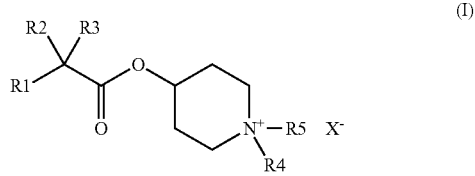

and a cosmetically or dermatologically acceptable carrier.

In formula (I), the radicals $R_1$ through $R_5$ and $X^-$ have the following meanings:

$R_4$ and $R_5$ independently represent H or $C_1$-$C_6$ alkyl;

$R_1$ and $R_3$ independently represent optionally substituted $C_3$-$C_8$ cycloalkyl, optionally substituted phenyl or optionally substituted saturated or unsaturated $C_1$-$C_6$ alkyl;

$R_2$ represents H, OH and OR, with R representing or $C_1$-$C_7$ alkyl (linear, branched, cyclic, saturated or unsaturated such as, e.g., methyl, ethyl, n-propyl, isopropyl, allyl, propargyl, n-butyl, cyclopentyl and cyclohexyl); and $X^-$ represents a cosmetically or dermatologically acceptable anion.

The compounds of formula (I) may, for example, be present as individual isomers (e.g., enantiomers), as any mixtures of isomers and as racemates.

Preferred meanings of $R_1$ through $R_5$ and X are as follows:

$R_4$ and $R_5$ $C_1$-$C_4$ alkyl, in particular $C_1$-$C_3$ alkyl, preferably methyl and ethyl and particularly preferably methyl; $R_4$ and $R_5$ are preferably identical;

$R_1$ optionally substituted $C_3$-$C_8$ cycloalkyl or optionally substituted phenyl, in particular (preferably unsubstituted) phenyl;

$R_3$ optionally substituted $C_3$-$C_8$ alkyl, $C_3$-$C_8$ cycloalkyl or optionally substituted phenyl; preferably $C_3$-$C_6$ alkyl, $C_3$-$C_6$ cycloalkyl or phenyl, particularly preferred (preferably unsubstituted) cyclopentyl, cyclohexyl, isopropyl, 2-butyl, 2-pentyl, 3-pentyl, 2-hexyl and 3-hexyl;

$R_2$ H, OH or OR, with R representing $C_1$-$C_3$ alkyl, in particular H or OH;

X halogen (fluorine, chlorine, bromine and iodine), sulfate, carbonate, ascorbate or phosphate, in particular halogen, preferably Cl, Br and I, even more preferably bromine.

Non-limiting specific examples of the various (cyclo)alkyl groups $R_1$ and $R_3$ through $R_5$ in unsubstituted form are as follows:

$R_4$ and $R_5$ methyl, ethyl, propyl, isopropyl, n-butyl, 2-butyl, sec-butyl, isobutyl, pentyl and hexyl;

$R_1$ cyclopropyl, cyclobutyl, cyclopentyl, cyclohexyl, cycloheptyl and cyclooctyl;

$R_3$ cyclopropyl, cyclobutyl, cyclopentyl, cyclohexyl, cycloheptyl, cyclooctyl, isopropyl, 2-butyl, 2-pentyl, 3-pentyl, 2-hexyl and 3-hexyl.

Exemplary substituents include halogen, in particular F, Cl and Br, hydroxyl (OH), $C_1$-$C_4$ alkoxy (e.g., methoxy and ethoxy), amino, mono($C_1$-$C_4$ alkyl)amino, di($C_1$-$C_4$ alkyl)amino, optionally substituted $C_1$-$C_5$ alkyl (e.g., methyl, ethyl, propyl, isopropyl, n-butyl, 2-butyl, isobutyl and tert-butyl), COOH and $SO_3H$. The cycloalkyl and phenyl groups can have one, two, three or even more substituents. Preferably these groups are unsubstituted.

In one aspect of the composition, the at least one compound of formula (I) may comprise a 4-[(2-cyclopentyl-2-hydroxyphenylacetyl)oxy]-1,1-dimethyl-piperidinium salt of formula

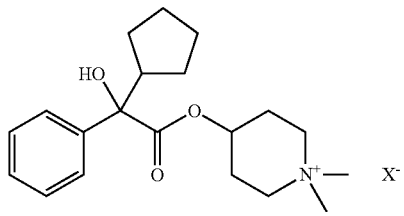

wherein $X^-$ is defined as above.

In another aspect of the composition, the at least one compound of formula (I) may comprise a 4-[(2-cyclohexyl-2-hydroxyphenylacetyl)oxy]-1,1-dimethyl-piperidinium salt of formula

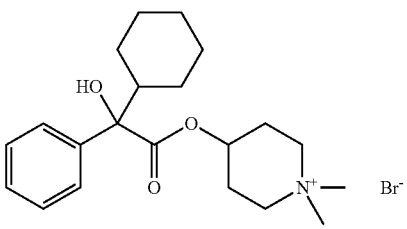

wherein $X^-$ is defined as above.

In yet another aspect, the composition according to the present invention may contain at least one salt of formula (I) in a concentration of from about 0.001% to about 15% by weight, based on the total weight of the composition. For example, the composition may contain at least one salt of formula (I) in a concentration of from about 0.05% to about 10% by weight, or in a concentration of from about 0.1% to about 5% by weight.

In another aspect, the composition of the present invention may comprise:

(a) one or more 4-[(2-cyclopentyl-2-hydroxyphenylacetyl)oxy]-1,1-dimethyl-piperidinium salts of formula

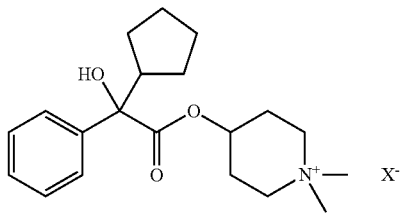

and/or
(b) one or more 4-{[2-(2-butyl)-phenylacetyl]oxy}-1,1-dimethyl-piperidinium salts (IUPAC name: 1,1-dimethyl-4-[(3-methyl-2-phenyl-pentanoyl)oxy]-piperidinium salts) of formula

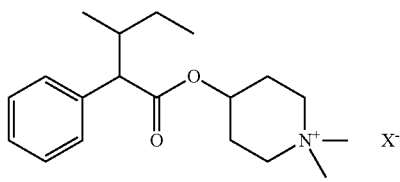

and/or
(c) one or more 4-[(2-cyclohexyl-2-hydroxyphenylacetyl)oxy]-1,1-dimethyl-piperidinium salts of formula

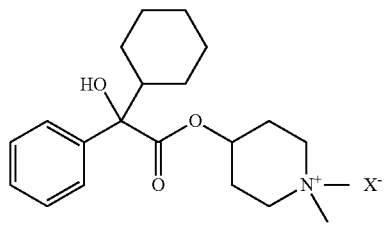

wherein $X^-$ is as defined above and preferably represents bromide.

In another aspect, the composition according to the present invention may be present in a form which is suitable for topical application. For example, the composition may be present in the form of a cream, a lotion, a gel, an ointment, a tincture, a skin oil, a milk, a balm, a bandage impregnated with the composition, a cloth impregnated with the composition, a textile impregnated with the composition, a pad impregnated with the composition, a spray, an aerosol, a roll-on, a stick, a soft solid, a powder or a powder spray.

In another aspect, the composition according to the present invention may be present in a form that is suitable for use as an antiperspirant.

In another aspect, the composition may further comprise at least one deodorizing substance.

In another aspect, the composition according to the present invention may further comprise an antiperspirant-active aluminum compound. For example, the at least one antiperspirant-active aluminum compound may be present in a concentration of from about 0.1% to about 30% by weight, e.g., in a concentration of from about 1% to about 15% by weight, based on the total weight of the composition. The antiperspirant-active aluminum compound may comprise, e.g., aluminum chlorohydrate, aluminum chloride and/or an aluminum zirconium compound.

In another aspect, the composition may be essentially free of antiperspirant-active substances that are different from a salt of formula (I). In particular, the composition may be substantially free of aluminum compounds.

In another aspect, the composition according to the present invention may be present in the form of a liquid or bar soap, an aerosol, a stick deodorant, a cream, a lotion, a deodorizing tincture, a deodorizing intimate cleansing agent, a deodorizing shampoo, a deodorizing shower or bath preparation, a deodorizing powder or a deodorizing powder spray and/or the composition may be present in combination with an aerosol container, a squeeze bottle, a pump device or a roll-on device.

The present invention also provides a method for reducing or inhibiting the formation of perspiration. The method comprises the application of an antiperspirant-effective amount of a composition according to the present invention as set forth above (including the different aspects thereof) onto (human) skin.

In one aspect of the method, the application of the composition may be carried out with the use of ultrasound, an iontophoresis apparatus, microchannels and/or microneedles.

The present invention also provides new compounds of the above formula (I), in particular 4-[2-cyclopentyl-2-hydroxyphenylacetyl)oxy]-1,1-dimethyl-piperidinium bromide of formula

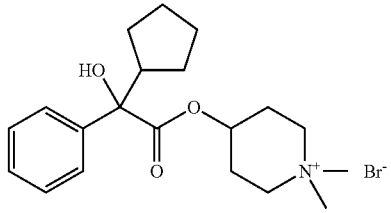 [SMILES: C[N+]1(C)CCC(OC(=O)C(O)(c2ccccc2)C2CCCC2)CC1 ; [Br-]]

and 4-[2-cyclohexyl-2-hydroxyphenylacetyl)oxy]-1,1-dimethyl-piperidinium bromide of formula

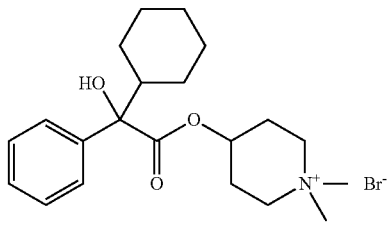 [SMILES: C[N+]1(C)CCC(OC(=O)C(O)(c2ccccc2)C2CCCCC2)CC1 ; [Br-]]

These compounds and in particular, the cyclopentyl compound are preferred compounds for use in the compositions and methods of the present invention.

DETAILED DESCRIPTION OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description making apparent to those skilled in the art how the several forms of the present invention may be embodied in practice.

As set forth above, particularly advantageous for the purposes of the present invention are compounds of formula

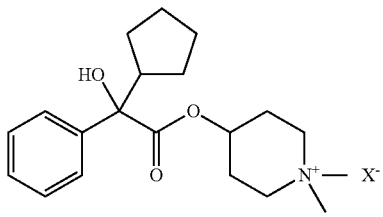

and of the formula

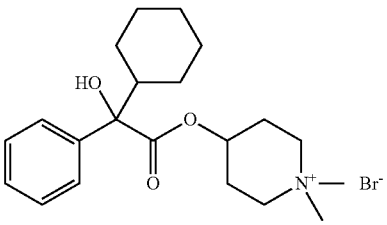 [SMILES: C[N+]1(C)CCC(OC(=O)C(O)(c2ccccc2)C2CCCCC2)CC1 ; [Br-]]

These particularly preferred phenylacetoxy piperidinium compounds, in the following referred to as 4-[(2-cyclopentyl-2-hydroxyphenylacetyl)oxy]-1,1-dimethyl-piperidinium salts and 4-[(2-cyclohexyl-2-hydroxyphenylacetyl)oxy]-1,1-dimethyl-piperidinium salts, are easy to incorporate in therapeutically active or cosmetic compositions.

Another preferred group of compounds comprises compounds in which $X^-$ in formula (I) is a cosmetically acceptable anion, preferably selected from bromide, iodide, chloride, fluoride, sulfate, carbonate, ascorbate, phosphate and mixtures thereof (bromide being particularly preferred), $R_4$ and $R_5$ are both methyl radicals, $R_3$ is a cyclopentyl, cyclohexyl or 2-butyl radical, $R_1$ is an unsubstituted phenyl radical and $R_2$ represents hydrogen or hydroxy.

Furthermore, the present invention comprises the use of one or more piperidinium compounds, preferably selected from 4-[(2-cyclopentyl-2-hydroxyphenylacetyl)oxy]-1,1-dimethyl-piperidinium salts, 4-[(2-cyclopentyl-2-hydroxyphenylacetyl)oxy]-1,1-dimethyl-piperidinium salts and 4-{[2-(2-butyl)-phenylacetyl]oxy}-1,1-dimethyl-piperidinium salts, in therapeutically active or cosmetic compositions.

Moreover, the present invention provides compositions that comprise one or more piperidinium compounds of formula (I), preferably 4-[(2-cyclopentyl-2-hydroxyphenylacetyl)oxy]-1,1-dimethyl-piperidinium salts, 4-[(2-cyclohexyl-2-hydroxyphenylacetyl)oxy]-1,1-dimethyl-piperidinium salts and/or 4-{[2-(2-butyl)-phenylacetyl]oxy}-1,1-dimethyl-piperidinium salts, and in particular preparations that can be applied topically, preferably cosmetic preparations, which comprise one or more of these compounds.

Preferred compounds of formula (I) include 4-[(2-cyclopentyl-2-hydroxyphenylacetyl)oxy]-1,1-dimethyl-piperidinium bromide of formula

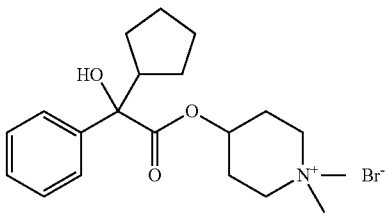 [SMILES: C[N+]1(C)CCC(OC(=O)C(O)(c2ccccc2)C2CCCC2)CC1 ; [Br-]]

In addition to the bromide, other salts, such as, e.g., iodide, chloride, fluoride, sulfate, carbonate, ascorbate or also other salts (e.g., determined by the preparation process) as well as optionally mixtures thereof can also be used. As anions, in particular those are chosen that can be used in cosmetics. Merely for the sake of simplicity in the following reference is made mainly to the above preferred bromide compound as representative of the compounds of the present invention.

Likewise particularly advantageous is the 4-{[2-(2-butyl)-2-phenylacetyl)oxy]}-1,1-dimethyl-piperidinium bromide of formula:

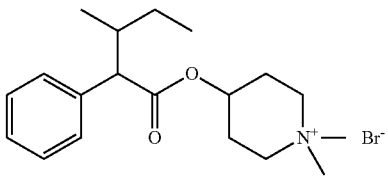 [SMILES: CCC(C)C(C(=O)OC1CC[N+](C)(C)CC1)c1ccccc1 ; [Br-]]

In this case, $R_4$ and $R_5$ in formula (I) are methyl radicals, $R_3$ is a 2-butyl radical, $R_1$ is an unsubstituted phenyl radical and $R_2$ represents hydrogen. $X^-$ represents bromide.

Likewise particularly advantageous is the 4-[(2-cyclohexyl-2-hydroxyphenylacetyl)oxy]-1,1-dimethyl-piperidinium bromide of formula:

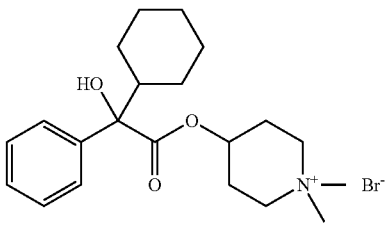 [SMILES: C[N+]1(C)CCC(OC(=O)C(O)(c2ccccc2)C2CCCCC2)CC1 ; [Br-]]

In this case, $R_4$ and $R_5$ in formula (I) are methyl radicals, $R_3$ is a cyclohexyl radical, $R_1$ is an unsubstituted phenyl radical and $R_2$ represents hydroxy. $X^-$ represents bromide.

Surprisingly, the piperidinium compounds used according to the present invention, in particular the 4-[(2-cyclopentyl-2-hydroxyphenylacetyl)oxy]-1,1-dimethyl-piperidinium salts, the 4-[(2-cyclopentyl-2-hydroxyphenylacetyl)oxy]-1,1-dimethyl-piperidinium salts and the 4-{[2-(2-butyl)-phenylacetyl]oxy}-1,1-dimethyl-piperidinium salts and especially, the bromides, show a very good efficacy in inhibiting perspiration. These compounds, in particular the 4-[(2-cyclopentyl-2-hydroxyphenylacetyl)oxy]-1,1-dimethyl-piperidinium salts and in particular the bromide, thus represent an alternative to the known agents for inhibiting or reducing perspiration.

The piperidinium compounds used according to the present invention, in particular, the 4-[(2-cyclopentyl-2-hydroxyphenylacetyl)oxy]-1,1-dimethyl-piperidinium salts, the 4-[(2-cyclopentyl-2-hydroxyphenylacetyl)oxy]-1,1-dimethyl-piperidinium salts and the 4-{[2-(2-butyl)-phenylacetyl]oxy}-1,1-dimethyl-piperidinium salts, can thus preferably be used for inhibiting or at least significantly reducing perspiration. They are easy to produce and may easily be incorporated into a plurality of therapeutically active or cosmetic formulations.

The piperidinium compounds used according to the present invention can be produced synthetically in a few steps from commercially available starting materials. A possible and preferred synthetic pathway, set forth by way of example for the 4-[(2-cyclopentyl-2-hydroxyphenylacetyl)oxy]-1,1-dimethyl-piperidinium salts, starts from methyl (2-cyclopentyl mandelate) and 4-hydroxy-N-methylpiperidine which are reacted in an esterification reaction. The last step of the synthesis is the conversion into the corresponding piperidinium compound, i.e., the quaternization of the nitrogen atom with reagents commonly used for this purpose, such as, e.g., methylbromide. The methyl (2-cyclopentyl mandelate) can, for example, in addition to many other conceivable variants, be prepared by a coupling reaction (e.g., a Grignard reaction) of, e.g., methylphenylglyoxylate (CAS No. 15205-55-0) with cyclopentyl halides. Through suitable starting compounds and suitable reaction conditions, the compound can also be prepared in enantiomerically pure or enantiomerically enriched form, respectively. The following reaction scheme illustrates the synthesis set forth above:

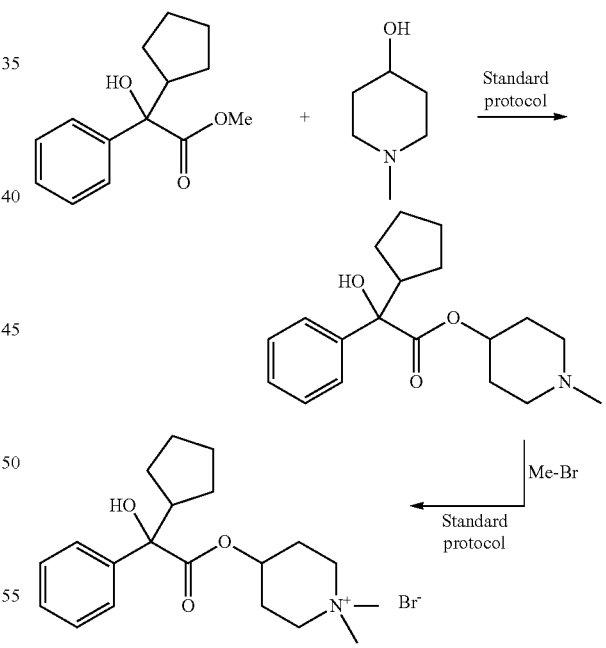

The present invention encompasses not only the above piperidinium compounds in general and in particular, the 4-[(2-cyclopentyl-2-hydroxyphenylacetyl)oxy]-1,1-dimethyl-piperidinium salts and the 4-[(2-cyclohexyl-2-hydroxyphenylacetyl)oxy]-1,1-dimethyl-piperidinium salts, but also encompasses the individual isomers and any desired mixtures thereof, even if for the sake of simplicity these compounds are discussed herein without any stereochemical information. The use of racemic mixtures is particularly preferred. If during a reaction a 1:1 mixture of enantiomers is formed, this is called a racemate or racemic mixture.

Surprisingly, the piperidinium compounds used according to the present invention, in particular the 4-[(2-cyclopentyl-2-hydroxyphenylacetyl)oxy]-1,1-dimethyl-piperidinium salts and the 4-[(2-cyclohexyl-2-hydroxyphenylacetyl)oxy]-1,1-dimethyl-piperidinium salts, and in particular the bromides, are toxicologically harmless, which could not necessarily be expected solely based on the chemical structural units thereof.

The applicability of in particular 4-[(2-cyclopentyl-2-hydroxyphenylacetyl)oxy]-1,1-dimethyl-piperidinium salts and 4-[(2-cyclohexyl-2-hydroxyphenylacetyl)oxy]-1,1-dimethyl-piperidinium salts in all conceivable product or application forms that permit any type of contact with humans, is particularly surprising.

4-[(2-Cyclopentyl-2-hydroxyphenylacetyl)oxy]-1,1-dimethyl-piperidinium salts and 4-[(2-cyclohexyl-2-hydroxyphenylacetyl)oxy]-1,1-dimethyl-piperidinium salts and in particular, the bromides show an effectiveness in reducing or even inhibiting perspiration.

Moreover, it is surprising and advantageous that the phenylacetoxy piperidinium salts and, in particular the 4-[(2-cyclopentyl-2-hydroxyphenylacetyl)oxy]-1,1-dimethyl-piperidinium salts, especially the bromide, are readily soluble in water. Incorporation into known water-based compositions is thus possible and preferred.

In addition to the medical application forms as a therapeutic agent, i.e., as a pharmaceutical preparation, the use of the present piperidinium compounds in cosmetics is possible and preferred.

In particular 4-[(2-cyclopentyl-2-hydroxyphenylacetyl)oxy]-1,1-dimethyl-piperidinium bromide can therefore be used as a therapeutic agent, in a pharmaceutical preparation and here in particular for reducing or inhibiting the formation of perspiration.

In the present specification and the appended claims the terms "composition" and "agent" include all application forms, preparations, media or substances that can be used at, on, in and/or with objects, in methods and/or for application on human skin.

The latter application forms are summarized herein as topical application forms and comprise in particular all administration and application forms for external application to human skin. Topical application is therefore preferred and comprises topical external use or application, such as the application as cream, lotion, gel, ointment, tincture, skin oil, milk, balm, by means of plaster, cloth, textile, pad, as spray, as an atomizer, aerosol, roll-on, stick, soft solid, powder, powder spray and other known forms of topical application, such as, e.g., insertion into the skin by an iontophoresis apparatus, ultrasound, microchannels or microneedles and the like. With the latter methods, a distinct reinforcement of penetration is achieved, which can lead to an intensified effect.

The piperidinium compounds according to the present invention, preferably in the application forms set forth above, and as readily water-soluble substances can be mixed in relatively large amounts and with the usual cosmetic production methods into cosmetic and/or dermatological preparations.

In particular the 4-[(2-cyclopentyl-2-hydroxyphenylacetyl)oxy]-1,1-dimethyl-piperidinium salts and the 4-[(2-cyclohexyl-2-hydroxyphenylacetyl)oxy]-1,1-dimethyl-piperidinium salts, especially the bromides, can therefore preferably be used as cosmetics or as constituents of cosmetic compositions.

The concentration of the piperidinium compounds, in particular the 4-[(2-cyclopentyl-2-hydroxyphenylacetyl)oxy]-1,1-dimethyl-piperidinium salts and the 4-[(2-cyclohexyl-2-hydroxyphenylacetyl)oxy]-1,1-dimethyl-piperidinium salts, in a composition, individually or as mixtures, usually is at least about 0.001% by weight, preferably at least about 0.05% by weight, particularly preferably at least about 0.1% by weight, but usually not higher than about 15% by weight, preferably not higher than about 10% by weight, particularly preferably not higher than about 5% by weight, based on the total weight of the composition.

Particularly the 4-[(2-cyclopentyl-2-hydroxyphenylacetyl)oxy]-1,1-dimethyl-piperidinium salts and the 4-[(2-cyclohexyl-2-hydroxyphenylacetyl)oxy]-1,1-dimethyl-piperidinium salts, preferably the bromides, can be used individually or in mixtures, particularly in the form of a topical agent for the effective reduction of perspiration.

It is furthermore preferred according to the present invention for the topical compositions to not include pharmaceutical products or agents with a therapeutic effect. Consequently, the compositions of the present invention preferably do not contain therapeutic agents. However, if therapeutic agents are included in the compositions, they are preferably selected from those which are conventionally administered by topical application to the skin, such as, e.g., antimycotics.

The use of the piperidinium compounds used according to the present invention, in particular of the 4-[(2-cyclopentyl-2-hydroxyphenylacetyl)oxy]-1,1-dimethyl-piperidinium salts and the 4-[(2-cyclohexyl-2-hydroxyphenylacetyl)oxy]-1,1-dimethyl-piperidinium salts, is preferred also for wound and skin care, as constituents of detersive compositions and cleansing compositions, in (preferably decorative) cosmetics, and in particular, in deodorant/antiperspirant compositions.

As a rule, cosmetics are creams, ointments and other compositions which are applied to the skin. They serve either to accent individual parts of the body, mostly on the face (lipstick, eye shadow) or for covering, for example, scars, acne etc. In general, cosmetics are used for beautification, but not for medicinal purposes.

Due to their antihidrotic effect, in particular the 4-[(2-cyclopentyl-2-hydroxyphenylacetyl)oxy]-1,1-dimethyl-piperidinium salts and the 4-[(2-cyclohexyl-2-hydroxyphenylacetyl)oxy]-1,1-dimethyl-piperidinium salts, preferably the bromides, can be used advantageously in deodorants and antiperspirants.

Surprisingly, the present invention provides a remedy for the described disadvantages of the known antiperspirant agents, in particular aluminum compounds, since, due to the antihidrotic effect of, for example, the 4-[(2-cyclopentyl-2-hydroxyphenylacetyl)oxy]-1,1-dimethyl-piperidinium salts and the 4-[(2-cyclohexyl-2-hydroxyphenylacetyl)oxy]-1,1-dimethyl-piperidinium salts, the amount of antiperspirant agents used, such as ACH, can be reduced or completely eliminated.

Moreover, particularly the 4-[(2-cyclopentyl-2-hydroxyphenylacetyl)oxy]-1,1-dimethyl-piperidinium salts show a good tolerance and preferably do not significantly inhibit the effectiveness of antiperspirant agents.

Another possible advantage associated with the present invention is that in particular 4-[(2-cyclopentyl-2-hydroxyphenylacetyl)oxy]-1,1-dimethyl-piperidinium salts and 4-[(2-cyclohexyl-2-hydroxyphenylacetyl)oxy]-1,1-dimethyl-piperidinium salts, preferably the bromides, can be used in deodorant/antiperspirant compositions as antimicrobial substances for reducing odor both in combination with standard deodorant/antiperspirant agents such as, e.g., aluminum chlorohydrate or other aluminum salts and also completely without such standard agents.

It is therefore possible to provide deodorant/antiperspirant compositions which preferably comprise from about 0.01 to about 25% by weight of aluminum-containing antiperspirant agents, in particular aluminum chlorohydrates, in combination with the 4-[(2-cyclopentyl-2-hydroxyphenylacetyl)oxy]-1,1-dimethyl-piperidinium salts and other piperidinium salts of the present invention.

In addition there is the extremely advantageous property of good water solubility of the compounds used according to the present invention.

Due to their advantageous properties, the cosmetic preparations of the present invention can be employed, for example, in the form of aerosols, thus preparations that can be sprayed from aerosol containers, squeeze bottles or by a pump device, or in the form of liquid compositions that can be applied by means of roll-on devices or with a brush, as deodorant sticks and in the form of W/O or O/W emulsions, e.g., creams or lotions, that can be applied from normal bottles or containers, or in the form of liquid or bar soaps. Furthermore, the cosmetic deodorants can advantageously be present in the form of deodorizing tinctures, deodorizing feminine hygiene cleansing agents, deodorizing shampoos, deodorizing shower or bath preparations, deodorizing powders or deodorizing powder sprays.

In addition to these preparations and application forms, those of skill in the art are also aware of modern technologies for the formulation of active ingredients for optimizing the parameters stability, solubility, control of release and bioavailability. The modern formulation technologies include, for example, microencapsulation and nanoencapsulation (matrix principle), membrane systems (e.g., liposomes) as well as cyclodextrins. Some of these methods are described, e.g., in the textbook Pharmazeutische Technologie: Moderne Arzneiformen, 2. ed., Wiss. Verl.-Ges. 1998 by Rainer H. Müller and Gesine H. Hildebrand, the entire disclosure whereof is incorporated by reference herein.

Non-limiting examples of materials for these formulation technologies include waxes, lipids, phospholipids, natural and synthetic polymers and also cyclodextrins. The dimensions of these systems are usually of the order of from about 0.01 μm to about 50 μm.

Likewise preferred is the use of the piperidinium compounds according to the present invention, in particular the 4-[(2-cyclopentyl-2-hydroxyphenylacetyl)oxy]-1,1-dimethyl-piperidinium salts and the 4-[(2-cyclohexyl-2-hydroxyphenylacetyl)oxy]-1,1-dimethyl-piperidinium salts, in wound dressings and skin care and as constituents of detersive preparations and cleansing compositions.

Of course, it is known to those of skill in the art that cosmetic preparations are usually inconceivable without the usual auxiliary agents and additives. The cosmetic preparations according to the invention can accordingly further contain cosmetic auxiliary agents as are conventionally used in such preparations; for example builders, preservatives, stabilizers, fillers, perfumes, pigments with/without coloring effect, thickeners, surface-active substances, emolients, moisturizers and/or humectants, anti-inflammatory substances, additional active agents, such as vitamins or proteins, light protection agents, insect repellents, bactericides, virucides, water, salts, antimicrobial, proteolytic or keratolytic substances, medicaments or other customary constituents of a cosmetic or dermatological formulation, such as alcohols, polyols, polymers, foam stabilizers, organic solvents and also electrolytes.

Cosmetic and/or dermatological preparations according to the present invention can also be present as gels which in addition to an effective amount of the compounds used according to the present invention and solvents conventionally used therefor, usually and preferably water, also contain organic and/or inorganic thickeners. Furthermore, these thickeners are a constituent of cosmetic emulsions.

As emulsifiers for producing the preparations according to the present invention, which may advantageously be applied to the desired areas of the skin as liquid or solid preparations, and which can be used in the preparations in small amounts, for example, from about 1% to about 6% by weight, nonionic types have proven to be suitable, such as polyoxyethylene fatty alcohol ethers, for example cetostearyl alcohol polyethylene glycol ether having 12 or 20 ethylene oxide units per molecule, cetostearyl alcohol and sorbitan esters and sorbitan ester-ethylene oxide compounds (for example, sorbitan monostearate and polyoxyethylene sorbitan monostearate), and long-chain higher molecular weight waxy polyglycol ethers. In addition, however, a large number of other emulsifiers or emulsifier mixtures are also suitable, which are normally used in cosmetic preparations. Non-limiting examples thereof include glyceryl stearate citrate, PEG 40 stearate or also polyglyceryl(3)-methylglucose distearate, stearic acid, steareth-2, steareth-21, glyceryl isostearate isoceteth-20 or also ceteareth-20.

The oil (lipid) phase of the preparations which are preferred according to the present invention is advantageously chosen from esters of saturated and/or unsaturated, branched and/or unbranched alkanecarboxylic acids having a chain length of from about 3 to about 30 carbon atoms and saturated and/or unsaturated, branched and/or unbranched alcohols having a chain length of from about 3 to about 30 carbon atoms, from esters of aromatic carboxylic acids and saturated and/or unsaturated, branched and/or unbranched alcohols having a chain length of from about 3 to about 30 carbon atoms. Such ester oils can then advantageously be chosen, e.g., from isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, and synthetic, semi-synthetic and natural mixtures of such esters, e.g., jojoba oil.

Furthermore, the oil phase can be advantageously chosen from branched and unbranched hydrocarbons and hydrocarbon waxes, silicone oils, dialkyl ethers, the group of saturated or unsaturated, branched or unbranched alcohols, and fatty acid triglycerides, namely the triglycerol esters of saturated and/or unsaturated, branched and/or unbranched alkanecarboxylic acids having a chain length of from about 8 to about 24, in particular from about 12 to about 18 carbon atoms. The fatty acid triglycerides can, for example, be advantageously chosen from synthetic, semi-synthetic and natural oils, e.g., olive oil, sunflower oil, soya oil, peanut oil, rapeseed oil, almond oil, palm oil, coconut oil, palm kernel oil and the like.

Any blends of such oil and wax components can also be used advantageously for the purposes of the present invention.

The oil phase can advantageously also contain cyclic or linear silicone oils or can consist entirely of such oils, although it is preferable to use an additional content of other oil phase components in addition to the silicone oil or silicone oils. Cyclomethicone (octamethylcyclotetrasiloxane) or dimethicone is advantageously used as the silicone oil for use according to the present invention. However, other silicone oils can also be advantageously used for the purposes of the present invention, for example hexamethylcyclotrisiloxane, polydimethylsiloxane or poly(methylphenylsiloxane).

Advantageously, the concentration of the oil phase is from about 1% to about 50% by weight, based on the total weight of the preparations, preferably from about 2.5% to about 30% by weight, in particular preferably from about 5% to about 15% by weight.

Gelling agents, also called thickeners, are macromolecules which have a largely linear structure and have intermolecular forces of interaction which permit secondary and primary valence bonds between the individual molecules and thus the formation of a network-like structure. Some of them are water-soluble natural or synthetic polymers which form gels or viscous solutions in aqueous systems. They increase the viscosity of the water by either binding water molecules (hydration), or else by absorbing and encapsulating the water into their interwoven macromolecules, at the same time restricting the mobility of the water. Such water-soluble polymers represent a large group of chemically very different natural and synthetic polymers whose common feature is their solubility in water or aqueous media. A prerequisite for this is that these polymers have a number of hydrophilic groups sufficient for the solubility in water and are not too strongly crosslinked. The hydrophilic groups may be non-ionic, anionic or cationic in nature.

Advantageous thickeners for cosmetic preparations are, for example, copolymers of $C_{10-30}$ alkyl acrylates and one or more monomers of acrylic acid, methacrylic acid or esters thereof. The INCI designation for such compounds is "acrylates/C 10-30 alkyl acrylate crosspolymer." Particularly advantageous are the Pemulen® grades TR1, TR2 and TRZ by Goodrich (Noveon).

Carbopols are also advantageous gelling agents for preparations according to the invention. Carbopols are polymers of acrylic acid, in particular also acrylate-alkyl acrylate copolymers. Advantageous polymers are, for example, the grades 980, 981, 984, 1342, 1382, 2984 and 5984, likewise the ETD grades 2001, 2020, 2050 and Carbopol Ultrez 10, PVM/MA decadiene crosspolymer (trade name Stabileze 06), polyglyceryl methacrylate, and polyacrylamide. Also advantageous gelling agents for such preparations are xanthan gum, polyvinylpyrrolidone, cellulose derivatives, in particular cellulose ethers, such as, for example, hydroxypropylmethylcellulose, starch and starch derivatives, hyaluronic acid, carob seed flour, silica and aluminum silicates.

The thickener usually is contained in a gel, a dispersion, an emulsion and the like in a concentration of from about 0.01% to about 5% by weight, preferably from about 0.1% to about 2% by weight, based on the total weight of the composition.

The AMPS polymers may be commercially available as 100% active substance or as inverse thickeners.

EXAMPLES

Cross-linked AMPS copolymers, powder form:
Aristoflex AVC (ammonium acryloyldimethyltaurate/VP copolymer, Clariant) Aristoflex HMB (ammonium acryloyldimethyltaurate/beheneth-25 methacrylate copolymer, Clariant)
Cross-linked AMPS copolymers, inverse thickeners:
Simulgel (Seppic): hydroxyethyl acrylate/sodium acryloyldimethyl taurate copolymer/squalane/polysorbate
Advantageous polymers for use in the present invention are described, for example, in DE 100 29 462 A1, the entire disclosure whereof is incorporated by reference herein.

Ammonium acryloyldimethyltaurate/VP copolymer is a preferred acrylamidomethylpropyl sulfonic acid polymer for use in the present invention.

It may be preferred according to the present invention to add complexing agents to the described preparations. Complexing agents are auxiliaries known per se in cosmetology and galenic medicine. Complexing agents, in particular chelating agents, form complexes with metal atoms; in the presence of one or more polybasic complexing agents, i.e. chelating agents, these complexes represent metallacycles. Chelating agents are compounds in which an individual ligand occupies more than one coordination site on a central atom. In this case, therefore, compounds which are normally linear are closed as a result of complex formations via a metal atom or ion to form rings. The number of bonded ligands depends on the coordination number of the central metal. A prerequisite for chelate formation is that the compound which reacts with the metal contains two or more atomic groups which act as electron donors.

The complexing agent(s) can advantageously be chosen from customary compounds, preference being given to at least one substance selected from tartaric acid and anions thereof, citric acid and anions thereof, aminopolycarboxylic acids and anions thereof (such as, for example, ethylenediaminetetraacetic acid (EDTA) and anions thereof and nitrilotriacetic acid (NTA) and anions thereof.

The complexing agent(s) is/are advantageously present in cosmetic or dermatological preparations in amounts of from about 0.01% to about 10% by weight, preferably from about 0.05% to about 10% by weight, particularly preferably from about 0.1% to about 1.0% by weight, based on the total weight of the preparations.

Advantageous preservatives for the purposes of the present invention are, for example, benzyl alcohol, sorbic acid and salts thereof, formaldehyde donors (such as, for example, diazolidinyl urea (trade name Germall II from ISP), imidazolidinyl urea (trade name Germall 115) or DMDM hydantoin, which is available, for example, under the trade name Glydant™ from Lonza), methyl isothiazolinone and corresponding derivatives (trade name Kathon CG), iodopropynyl butylcarbamates (e.g., those available under the trade names Glycacil-L, Glycacil-S from Lonza and/or Dekaben LMB from Jan Dekker), parabens (i.e., alkyl p-hydroxybenzoates, such as methyl, ethyl, propyl, isopropyl and/or butyl paraben), phenoxyethanol, ethanol, triclosan, benzoic acid and the like. In addition, according to the present invention, the preservative system usually also advantageously comprises substances that improve the effectiveness of classic preservatives, such as, for example, hexanediol, pentanediol, butylene glycol and methylpropanediol.

It is likewise advantageous to add antioxidants to the preparations of the present invention. According to the invention, all antioxidants which are suitable and/or customary for cosmetic and/or dermatological applications can be used as favorable antioxidants.

The concentration of the antioxidants (one or more compounds) in the preparations is preferably from about 0.001% to about 30% by weight, particularly preferably from about 0.05% to about 20% by weight, in particular from about 1% to about 10% by weight, based on the total weight of the preparation.

According to the invention it is also possible and advantageous, to use UV-protective substances that absorb UV radiation in the UVB range. The total concentration of such filter substances may preferably be from about 0.1% by weight to about 30% by weight, based on the total weight of the composition. Commercially available water-soluble or oil-soluble UVB filters are preferred. It can also be advantageous to use in preparations according to the present invention UVA filters which are usually contained in cosmetic and/or dermatological preparations. The same amounts can be used as those listed for UVB filters.

Cosmetic and/or dermatological preparations according to the invention can also contain inorganic pigments that are customarily used in cosmetics for protecting the skin against UV rays. These are usually oxides of titanium, zinc, iron, zirconium, silicon, manganese, aluminum and mixtures thereof. Particular preference is given to pigments based on titanium dioxide, $TiO_2$, or zinc oxide, $ZnO$. The amounts given for the above combinations can be used.

Suitable propellants for cosmetic and/or dermatological formulations according to the invention which can be sprayed from aerosol containers include the customary known readily volatile, liquefied propellants, for example hydrocarbons (propane, butane, isobutane), which can be employed individually or as mixtures. Compressed air can also advantageously be used.

Of course, one of skill in the art is aware that there are propellant gases which are nontoxic per se and would in principle be suitable for realizing the present invention in the form of aerosol preparations, but which nevertheless should be avoided because of their unacceptable impact on the environment or other accompanying circumstances, in particular fluorocarbons and chlorofluorocarbons (CFCs).

Cosmetic or dermatological compositions of the present invention may also contain clay minerals such as sheet silicates and/or silicas as they are often used as suspending aids in oil containing cosmetic deodorants and antiperspirants.

Advantageous sheet silicates, optionally in modified form, for the purposes of the present invention include montmorillonite, kaolinite, ilite, beidellite, nontronite, saponite, hectorite, bentonite and smectite. Non-limiting specific examples of suitable sheet silicates include:

| | |
|---|---|
| Montmorillonite or simplified | $Na_{0.33}((Al_{1.67}Mg_{0.33})(OH)_2(Si_4O_{10}))$ $Al_2O_3*4SiO_2*H_2O*nH_2O$ |
| Kaolinite | $Al_2(OH)_4(Si_2O_5)$ |
| Ilite | $(K,H_3O)_y(Mg_3(OH)_2(Si_{4-y}Al_yO_{10}))$ and $(K,H_3O)_y(Al_2(OH)_2(Si_{4-y}Al_yO_{10}))$ y = 0.7-0.9 |
| Beidellite | $(Ca,Na)_{0.3}(Al_2(OH)_2(Al_{0.5}Si_{3.5}O_{10}))$ |
| Nontronite | $Na_{0.33}(Fe_2(OH)_2(Al_{0.33}Si_{3.67}O_{10}))$ |
| Saponite | $(Ca,Na)_{0.33}((Mg,Fe)_3(OH)_2(Al_{0.33}Si_{3.67}O_{10}))$ |
| Hectorite | $Na_{0.33}((Mg,Li)_3(OH,F)_2(Si_4O_{10}))$ |

Montmorillonite constitutes the main mineral of the naturally occurring bentonites.

Sheet silicates are well documented in the literature, see, e.g., the text books "Lehrbuch der Anorganischen Chemie", A. F. Hollemann, E. Wiberg and N. Wiberg, 91.-100. ed., Walter de Gruyter-Verlag 1985, passim, and "Lehrbuch der Anorganischen Chemie", H. Remy, 12. ed., Akademische Verlagsgesellschaft, Leipzig 1965, passim. The sheet structure of montmorillonite is documented in, for example, Römpps Chemie-Lexikon, Franckh'sche Verlagshandlung W. Keller & Co., Stuttgart, 8. ed., 1985, pp. 2668f. The entire disclosures of these books are incorporated by reference herein.

Preparations according to the present invention may also contain one or more surfactants. Surfactants are amphiphilic substances which can dissolve organic, non-polar substances in water. As a result of their specific molecular structure having at least one hydrophilic molecular moiety and one hydrophobic molecular moiety, they are able to reduce the surface tension of the water, wet the skin, facilitate the removal and dissolution of soiling, facilitate rinsing and, if desired, control foaming.

The hydrophilic moieties of a surfactant molecule are mostly polar functional groups, for example $—COO^-$, $—OSO_3^{2-}$, $—SO_3^-$, while the hydrophobic moieties are usually non-polar hydrocarbon radicals. Surfactants are generally classified according to the type and charge of the hydrophilic molecular moiety. In this regard, it is possible to differentiate between four groups:

anionic surfactants,
cationic surfactants,
amphoteric surfactants and
nonionic surfactants.

The following are advantageous and non-limiting examples of compositions of the present invention.

Example 1

Alcoholic Roll-Ons

Transparent

| | I | II | III |
|---|---|---|---|
| Raw Material (INCI) | % by weight | | |
| Denaturated alcohol | 20.000 | 30.000 | 20.000 |
| Hydroxyethylcellulose | 0.400 | 0.300 | 0.400 |
| Polyethylene glycol 400 | 3.000 | 2.000 | 3.000 |
| Polyethylene glycol (2000) hydrogenated castor oil | 2.000 | 3.000 | 2.000 |
| Avocado oil | 0.500 | 0.100 | 0.500 |
| 4-[(2-Cyclopentyl-2-hydroxyphenylacetyl)oxy]-1,1-dimethyl-piperidinium bromide | — | 0.30 | 0.50 |
| 4-[(2-Cyclohexyl-2-hydroxyphenylacetyl)oxy]-1,1-dimethyl-piperidinium bromide | 0.50 | | |
| Perfume, antioxidants | q.s. | q.s. | q.s. |
| Water | ad 100.000 | ad 100.000 | ad 100.000 |

Example 2

Deodorant Creams Macroemulsions

| | I | II | III | IV |
|---|---|---|---|---|
| Raw Material (INCI) | % by weight | | | |
| Polyethylene glycol(21)stearyl ether | 2.000 | 1.500 | 1.000 | 2.500 |
| Polyethylene glycol(2)stearyl ether | 2.500 | 2.500 | 2.200 | 1.500 |
| Polypropylene glycol(15)stearyl ether | 3.000 | 4.000 | 4.000 | 3.000 |
| Coco fatty acid 2-ethylhexyl ester | — | — | — | 1.000 |
| $Na_3HEDTA$ (20% aqueous solution) | 1.500 | 1.500 | 1.500 | 1.500 |
| Avocado oil | 0.100 | 0.100 | 0.100 | 0.100 |
| Perfume, antioxidants | q.s. | q.s. | q.s. | q.s. |
| 4-[(2-Cyclopentyl-2-hydroxyphenylacetyl)oxy]-1,1-dimethyl-piperidinium bromide | 0.05 | 0.3 | 0.1 | 0.5 |
| Water | ad 100.000 | ad 100.000 | ad 100.000 | ad 100.000 |

-continued

| Raw Material (INCI) | V | VI | VII | VIII |
|---|---|---|---|---|
| | % by weight | | | |
| Polyethylene glycol(21)stearyl ether | 2.000 | 1.000 | 3.000 | 1.500 |
| Polyethylene glycol(2)stearyl ether | 2.000 | 3.000 | 2.500 | 3.000 |
| Polypropylene glycol(15)stearyl ether | 3.000 | 3.000 | 3.000 | 3.000 |
| Coco fatty acid 2-ethylhexyl ester | — | — | 1.000 | — |
| $Na_3$HEDTA (20% aqueous solution) | 1.500 | 1.500 | 1.500 | 1.500 |
| Avocado oil | 0.100 | 0.100 | 0.100 | 0.100 |
| Perfume, antioxidants | q.s. | q.s. | q.s. | q.s. |
| 4-[(2-cyclopentyl-2-hydroxyphenylacetyl)oxy]-1,1-dimethyl-piperidinium bromide | 0.01 | — | 0.2 | — |
| 4-[(2-cyclohexyl-2-hydroxyphenylacetyl)oxy]-1,1-dimethyl-piperidinium bromide | | 0.5 | | 0.5 |
| 4-[(2-(2-butyl)-2-hydroxyphenylacetyl)oxy]-1,1-dimethyl-piperidinium bromide | | | | |
| Water | ad 100.000 | ad 100.000 | ad 100.000 | ad 100.000 |

Example 3

O/W Emulsion

| Raw Material (INCI) | I | II |
|---|---|---|
| | % by weight | |
| Polyglyceryl-3-methyl glucose distearate | 2.00 | 2.00 |
| Stearyl alcohol | 2.00 | 2.00 |
| $C_{12-15}$ Alkyl benzoate | 3.00 | 3.00 |
| Butylene glycol dicaprylate/dicaprate | 2.00 | 2.00 |
| Cyclomethicone | 3.00 | 3.00 |
| Hydrogenated polydecene | 2.00 | 2.00 |
| Dimethylpolysiloxane (dimethicone) | 1.00 | 1.00 |
| Petrolatum | 1.00 | 1.00 |
| $TiO_2$ | 1.00 | 1.00 |
| 4-[(2-Cyclopentyl-2-hydroxyphenylacetyl)oxy]-1,1-dimethyl-piperidinium bromide | 2.00 | — |
| 4-[(2-cyclohexyl-2-hydroxyphenylacetyl)oxy]-1,1-dimethyl-piperidinium bromide | — | 1.00 |
| Allantoin | 0.10 | 0.10 |
| Phenoxyethanol | 0.40 | 0.40 |
| Iodopropynylbutyl carbamate | 0.05 | 0.05 |
| p-Hydroxybenzoic alkyl ester (paraben) | 0.20 | 0.20 |
| Xanthan gum | 0.10 | 0.10 |
| Carbomer | 0.10 | 0.10 |
| Butylene glycol | 3.00 | 3.00 |
| Additives (talc, BHT) | 0.50 | 0.50 |
| Perfume | q.s. | q.s. |
| Water | ad 100 | ad 100 |

Example 4

| Raw Material (INCI) | I | II |
|---|---|---|
| | % by weight | |
| Polyglyceryl-3-methyl glucose distearate | 3.00 | 3.00 |
| Cetyl alcohol | 1.00 | 1.00 |
| Cyclomethicone | 3.00 | 3.00 |
| Dicapryl ether | 2.00 | 2.00 |
| Paraffinum liquidum | 3.00 | 3.00 |
| Ethylenediaminetetraacetic acid trisodium | 0.10 | 0.10 |
| Carbomer | 0.10 | 0.10 |
| Hydroxypropylmethylcellulose | 0.3 | 0.3 |
| 4-[(2-Cyclopentyl-2-hydroxyphenylacetyl)oxy]-1,1-dimethyl-piperidinium bromide | 0.50 | — |
| 4-[(2-(2-butyl)-2-hydroxyphenylacetyl)oxy]-1,1-dimethyl-piperidinium bromide | — | 0.05 |
| Aluminum chlorohydrate | 5.00 | 5.00 |
| Glycerin | 3.00 | 3.00 |
| NaOH | q.s. | q.s. |
| Preservatives | q.s. | q.s. |
| Perfume | q.s. | q.s. |
| Water | ad 100 | ad 100 |

Example 5

| Raw Material (INCI) | I | II |
|---|---|---|
| | % by weight | |
| Polyglyceryl-3-methyl glucose distearate | 3.00 | 3.00 |
| Sorbitan stearate | 1.00 | 1.00 |
| $C_{12-15}$ Alkyl benzoate | 2.00 | 2.00 |
| Ethylhexyl coconut fatty acid ester | 5.00 | 5.00 |
| Octamethyltetrasiloxane (cyclomethicone) | 5.00 | 5.00 |
| Polydecene | 1.00 | 1.00 |
| 4-[(2-Cyclopentyl-2-hydroxyphenylacetyl)oxy]-1,1-dimethyl-piperidinium bromide | 1.00 | — |
| 4-[(2-Cyclohexyl-2-hydroxyphenylacetyl)oxy]-1,1-dimethyl-piperidinium bromide | — | 1.00 |
| Tocopherol | 0.10 | 0.10 |
| EDTA | 0.20 | 0.20 |
| para-Hydroxybenzoic alkyl ester (paraben) | 0.40 | 0.40 |
| Methylpropanediol | 3.00 | 3.00 |
| Ethanol, denatured | 2.00 | 2.00 |
| Xanthan gum | 0.2 | 0.2 |
| Carbomer | 0.1 | 0.1 |
| Glycerin | 5.00 | 5.00 |
| Filler/additives (distarch phosphate, talc) | 2.00 | 2.00 |
| Perfume | q.s. | q.s. |
| Water | ad 100 | ad 100 |

Example 6

O/W Emulsion

| Raw Material (INCI) | I | II |
|---|---|---|
| | % by weight | |
| Glyceryl stearate citrate | 1.50 | 1.50 |
| Cetyl stearyl alcohol | 1.00 | 1.00 |
| Caprylic/capric triglyceride | 1.00 | 1.00 |
| Dicaprylcarbonate | 2.00 | 2.00 |
| Dimethylpolysiloxane, cyclic (dimethicone) | 4.00 | 4.00 |
| Carbopol | 0.15 | 0.15 |
| Acrylic acid/C10-30 alkylmethacrylate-copolymer | 0.25 | 0.25 |
| Dimethicone | 0.75 | 0.75 |
| Jojoba oil | 1.00 | 1.00 |
| Tocopheryl acetate | 0.75 | 0.75 |
| Glycerin | 10.00 | 10.00 |
| Ethanol | 1.00 | 1.00 |

-continued

| Raw Material (INCI) | I | II |
|---|---|---|
| | % by weight | |
| 4-[(2-Cyclopentyl-2-hydroxyphenylacetyl)oxy]-1,1-dimethyl-piperidinium bromide | 1.50 | — |
| 4-[(2-(2-butyl)-2-hydroxyphenylacetyl)oxy]-1,1-dimethyl-piperidinium bromide | — | 0.75 |
| Fillers/additives (distarch phosphate, BHT, talc, aluminum starch octenylsuccinate, cyclodextrin) | 1.00 | 1.00 |
| Perfume | q.s. | q.s. |
| Preservatives | q.s. | q.s. |
| Water | ad 100 | ad 100 | pH value adjusted to 6.0

Example 7

O/W Emulsion

| Raw material (INCI) | I | II |
|---|---|---|
| | % by weight | |
| Glyceryl stearate citrate | 3.00 | 3.00 |
| Stearyl alcohol | 1.00 | 1.00 |
| Caprylic/capric triglyceride | 1.00 | 1.00 |
| Octyldodecanol | 1.00 | 1.00 |
| Dicaprylether | 1.00 | 1.00 |
| 4-[(2-Cyclopentyl-2-hydroxyphenylacetyl)oxy]-1,1-dimethyl-piperidinium bromide | 0.50 | — |
| 4-[(2-Cyclohexyl-2-hydroxyphenylacetyl)oxy]-1,1-dimethyl-piperidinium bromide | — | 0.50 |
| Aluminum chlorohydrate | 3.00 | 3.00 |
| Carbomer | 0.15 | 0.15 |
| Glycerin | 3.00 | 3.00 |
| Perfume, preservatives, colorants, antioxidants, etc. | q.s. | q.s. |
| Water | ad 100 | ad 100 | pH value adjusted to 5.5

Example 8

O/W Emulsion

| Raw Material (INCI) | I | II |
|---|---|---|
| | % by weight | |
| Glyceryl stearate citrate | 3.00 | 3.00 |
| Cetyl stearyl alcohol | 1.00 | 1.00 |
| Cyclomethicone | 4.00 | 4.00 |
| Octyldodecanol | 1.00 | 1.00 |
| Dimethicone | 1.00 | 1.00 |
| 4-[(2-Cyclopentyl-2-hydroxyphenylacetyl)oxy]-1,1-dimethyl-piperidinium bromide | 1.00 | — |
| 4-[(2-Cyclohexyl-2-hydroxyphenylacetyl)oxy]-1,1-dimethyl-piperidinium bromide | — | 1.00 |
| Allantoin | 0.10 | 0.10 |
| Citric acid, sodium salt | 0.10 | 0.10 |
| Ethanol, denaturated | 3.00 | 3.00 |
| Aluminum zirconium chlorohydrate | 3.00 | 3.00 |
| Ammoniumacryloyl dimethyltaurate/VP copolymer | 0.30 | 0.30 |
| Glycerin | 10.00 | 10.00 |
| Additives (distarch phosphate, SiO₂, talc) | 0.1 | 0.1 |
| Perfume, preservatives, antioxidants, etc. | q.s. | q.s. |
| Water | ad 100 | ad 100 | pH value adjusted to 5.5

Example 9

O/W Emulsion

| Raw Material (INCI) | I | II | III |
|---|---|---|---|
| | % by weight | | |
| Glyceryl stearate citrate | 2.00 | 2.00 | 2.00 |
| Cetyl alcohol | 1.00 | 1.00 | 1.00 |
| Cyclomethicone | 3.00 | 3.00 | 3.00 |
| Jojoba oil | 0.30 | 0.30 | 0.30 |
| Paraffinium liquidum | 1.00 | 1.00 | 1.00 |
| 4-[(2-Cyclopentyl-2-hydroxyphenylacetyl)oxy]-1,1-dimethyl-piperidinium bromide | 1.00 | — | — |
| 4-[(2-(2-butyl)-2-hydroxyphenylacetyl)oxy]-1,1-dimethyl-piperidinium bromide | — | 0.75 | — |
| 4-[(2-Cyclohexyl-2-hydroxyphenylacetyl)oxy]-1,1-dimethyl-piperidinium bromide | — | — | 0.75 |
| Chitosan | 0.50 | 0.50 | 0.50 |
| Glycerin | 3.00 | 3.00 | 3.00 |
| Serine | 0.10 | 0.10 | 0.10 |
| Tocopherol acetate | 1.00 | 1.00 | 1.00 |
| Xanthan gum | 0.10 | 0.10 | 0.10 |
| Perfume, preservatives, colorants, antioxidants, etc. | q.s. | q.s. | q.s. |
| Water | ad 100 | ad 100 | ad 100 | pH value adjusted to 6.0

Example 10

Transparent Microemulsion

Roll-On

| Raw Material (INCI) | I | II |
|---|---|---|
| | % by weight | |
| Glycerol monoisostearate | 1.00 | 1.00 |
| Polyoxyethylene(20)isostearylether | 3.00 | 3.00 |
| Di-n-octylcarbonate | 3.00 | 3.00 |
| 2-Octyldodecanol | 2.00 | 2.00 |
| Glycerin | 3.00 | 3.00 |
| Jojoba oil | 0.10 | 0.10 |
| 4-[(2-Cyclopentyl-2-hydroxyphenylacetyl)oxy]-1,1-dimethyl-piperidinium bromide | 1.00 | — |
| 4-[(2-Cyclohexyl-2-hydroxyphenylacetyl)oxy]-1,1-dimethyl-piperidinium bromide | — | 1.00 |
| 2-Ethylhexyl glycerin ether | 0.50 | 0.50 |
| Chitosan | 0.50 | 0.50 |
| Perfume, antioxidants | q.s. | q.s. |
| Water | ad 100 | ad 100 |

Example 11

Translucent Microemulsion Atomizer

| Raw Material (INCI) | I | II |
|---|---|---|
| | % by weight | |
| Polyoxyethylene(20)cetylstearyl ether | 2.00 | 2.00 |
| Polyoxyethylene(12)cetylstearyl ether | 1.00 | 1.00 |

-continued

| Raw Material (INCI) | I | II |
|---|---|---|
| | % by weight | |
| Glycerin stearate | 2.50 | 2.50 |
| Cetylstearyl alcohol | 0.50 | 0.50 |
| Cetyl palmitate | 0.50 | 0.50 |
| Capryl/capric acid | 4.00 | 4.00 |
| Di-n-octylether | 8.00 | 8.00 |
| Glycerin | 3.00 | 3.00 |
| 4-[(2-Cyclopentyl-2-hydroxyphenylacetyl)oxy]-1,1-dimethyl-piperidinium bromide | 0.30 | — |
| 4-[(2-Cyclohexyl-2-hydroxyphenylacetyl)oxy]-1,1-dimethyl-piperidinium bromide | — | 0.30 |
| Pentanediol | 2.50 | 2.50 |
| Perfume, antioxidants | q.s. | q.s. |
| Water | ad 100 | ad 100 |

Example 12

Macroemulsion

Roll-On

| Raw Material (INCI) | I | II | III |
|---|---|---|---|
| | % by weight | | |
| Polyethyleneglycol(21)stearyl ether | 3.00 | 3.00 | 3.00 |
| Polyethyleneglycol(2)stearyl ether | 2.00 | 2.00 | 2.00 |
| Polypropyleneglycol(15)stearyl ether | 2.00 | 2.00 | 2.00 |
| EDTA | 0.10 | 0.10 | 0.10 |
| Avocado oil | 0.10 | 0.10 | 0.10 |
| Perfume, antioxidants | q.s. | q.s. | q.s. |
| 2-Ethylhexyl glycerin ether (octoxyglycerin) | 0.50 | 0.50 | 0.50 |
| Hexanediol | 3.00 | 3.00 | 3.00 |
| 4-[(2-Cyclopentyl-2-hydroxyphenylacetyl)oxy]-1,1-dimethyl-piperidinium bromide | 0.50 | — | — |
| 4-[(2-Cyclohexyl-2-hydroxyphenylacetyl)oxy]-1,1-dimethyl-piperidinium bromide | — | 0.50 | — |
| 4-[(2-(2-Butyl)-2-hydroxyphenylacetyl)oxy]-1,1-dimethyl-piperidinium bromide | — | — | 0.50 |
| Aluminum chlorohydrate | 3.00 | 3.00 | 3.00 |
| Water | ad 100 | ad 100 | ad 100 |

Example 13

Macroemulsion

Cream

| Raw Material (INCI) | I | II | III | IV |
|---|---|---|---|---|
| | % by weight | | | |
| Glycerin monostearate | 5.00 | 5.00 | 5.00 | 5.00 |
| Polyethyleneglycol(2000) monostearate | 2.00 | 2.00 | 2.00 | 2.00 |
| Stearyl alcohol | 3.00 | 3.00 | 3.00 | 3.00 |
| Cyclomethicone | 4.00 | 4.00 | 4.00 | 4.00 |
| Paraffin oil | 6.00 | 6.00 | 6.00 | 6.00 |
| EDTA | 0.20 | 0.20 | 0.20 | 0.20 |
| Chitosan | 0.50 | 0.50 | 0.50 | 0.50 |

-continued

| Raw Material (INCI) | I | II | III | IV |
|---|---|---|---|---|
| | % by weight | | | |
| 4-[(2-Cyclopentyl-2-hydroxyphenylacetyl)oxy]-1,1-dimethyl-piperidinium bromide | 0.80 | 0.75 | — | — |
| 4-[(2-Cyclohexyl-2-hydroxyphenylacetyl)oxy]-1,1-dimethyl-piperidinium bromide | — | — | 0.80 | — |
| 4-[(2-(2-Butyl)-2-hydroxyphenylacetyl)oxy]-1,1-dimethyl-piperidinium bromide | — | — | — | 0.80 |
| 2-Methylpropanediol | 3.00 | 3.00 | 3.00 | 3.00 |
| 2-Ethylhexyl glycerin ether | 0.50 | 0.50 | 0.50 | 0.50 |
| Antimycotic (clotrimazole or terbenafine) | — | 0.005 | — | — |
| Perfume, antioxidants | q.s. | q.s. | q.s. | q.s. |
| Water | ad 100 | ad 100 | ad 100 | ad 100 |

Example 14

Alcoholic Solution

Roll-On

| Raw Material (INCI) | I | II |
|---|---|---|
| | % by weight | |
| Alcohol, denat. | 25.00 | 25.00 |
| Hydroxyethylcellulose | 0.50 | 0.50 |
| Polyethyleneglycol 400 | 5.00 | 5.00 |
| Polyethyleneglycol (2000) hydrogenated castor oil | 4.00 | 4.00 |
| *Macadamia* oil | 0.20 | 0.20 |
| 4-[(2-Cyclopentyl-2-hydroxyphenylacetyl)oxy]-1,1-dimethyl-piperidinium bromide | 0.30 | — |
| 4-[(2-Cyclohexyl-2-hydroxyphenylacetyl)oxy]-1,1-dimethyl-piperidinium bromide | — | 0.30 |
| Pentanediol | 5.00 | 5.00 |
| 2-Ethylhexyl glycerin ether | 0.50 | 0.50 |
| Perfume, antioxidants | q.s. | q.s. |
| Water | ad 100 | ad 100 |

Example 15

Aerosol Spray Type A

| Raw Material (INCI) | I | II | III |
|---|---|---|---|
| | % by weight | | |
| 2-Octyldodecanol | 0.50 | 0.50 | 0.50 |
| 1,2-Propyleneglycol | 1.00 | 1.00 | 1.00 |
| Butyloctanoic acid | 0.25 | 0.25 | 0.25 |
| 4-[(2-Cyclopentyl-2-hydroxyphenylacetyl)oxy]-1,1-dimethyl-piperidinium bromide | 0.50 | 0.50 | — |
| 4-[(2-Cyclohexyl-2-hydroxyphenylacetyl)oxy]-1,1-dimethyl-piperidinium bromide | — | — | 0.50 |
| Antimycotic (clotrimazole or terbenafine) | — | 0.005 | — |
| Perfume | q.s. | q.s. | q.s. |
| Ethanol | ad 100 | ad 100 | ad 100 |

The liquid phase obtained by mixing together the respective constituents is poured into the aerosol container with a propane-butane mixture (2.7) in a ratio of 39:61.

Example 16

Aerosol Spray Type B

| Raw Material (INCI) | I | II | III |
|---|---|---|---|
| | % by weight | | |
| Aluminum chlorohydrate | 45.00 | 25.00 | 25.00 |
| Isopropyl palmitate | 25.00 | 30.00 | 30.00 |
| Cyclomethicone | ad 100.00 | 0.30 | 0.30 |
| Isoparaffin | — | ad 100.00 | ad 100.00 |
| Talc | — | 10.00 | 10.00 |
| 2-Hexyldecanoic acid | 0.25 | 0.30 | 0.25 |
| 4-[(2-Cyclopentyl-2-hydroxyphenylacetyl)oxy]-1,1-dimethyl-piperidinium bromide | 0.50 | 0.20 | — |
| 4-[(2-Cyclohexyl-2-hydroxyphenylacetyl)oxy]-1,1-dimethyl-piperidinium bromide | 0.25 | — | -.20 |
| Perfume | q.s. | q.s. | q.s. |

The liquid phase obtained by mixing together the respective constituents is poured into the aerosol container with a propane-butane mixture (2.7) in a ratio of 17:83.

Example 17

O/W Emulsion

| Raw Material (INCI) | I | II | III |
|---|---|---|---|
| | % by weight | | |
| Glycerystearate citrate | 2.00 | 2.00 | 2.00 |
| Cetylstearyl alcohol | 2.00 | 2.00 | 2.00 |
| Cyclomethicone | 3.00 | 3.00 | 3.00 |
| Caprylic acid/capric acid triglycerides | 4.00 | 4.00 | 4.00 |
| Octyldodecanol | 1.00 | 1.00 | 1.00 |
| Dimethicone | 2.00 | 2.00 | 2.00 |
| 4-[(2-Cyclopentyl-2-hydroxyphenylacetyl)oxy]-1,1-dimethyl-piperidinium bromide | 0.50 | — | — |
| 4-[(2-Cyclohexyl-2-hydroxyphenylacetyl)oxy]-1,1-dimethyl-piperidinium bromide | — | 0.50 | — |
| 4-[(2-(2-Butyl)-2-hydroxyphenylacetyl)oxy]-1,1-dimethyl-piperidinium bromide | — | — | 0.50 |
| Citric acid, sodium salt | 0.10 | 0.10 | 0.10 |
| Ethanol, denaturated | 3.00 | 3.00 | 3.00 |
| Ammoniumacryloyl dimethyltaurate/VP copolymer | 0.30 | 0.30 | 0.30 |
| Glycerin | 3.00 | 3.00 | 3.00 |
| Fillers (distarch phosphate, talc) | 0.10 | 0.10 | 0.10 |
| Perfume, fillers | q.s. | q.s. | q.s. |
| Water | ad 100 | ad 100 | ad 100 |

Example 18

O/W Emulsion

| Raw Material (INCI) | I | II |
|---|---|---|
| | % by weight | |
| PEG-40 stearate | 2.00 | 2.00 |
| Glyceryl stearate | 2.00 | 2.00 |
| Stearyl alcohol | 0.50 | 0.50 |
| Cetyl alcohol | 2.00 | 2.00 |
| $C_{12-15}$ Alkyl benzoate | 2.00 | 2.00 |
| Caprylic acid/capric acid triglycerides | 1.00 | 1.00 |
| Cyclomethicone | 3.00 | 3.00 |
| Dicaprylylcarbonate | 2.00 | 2.00 |
| 4-[(2-Cyclopentyl-2-hydroxyphenylacetyl)oxy]-1,1-dimethyl-piperidinium bromide | 0.75 | — |
| 4-[(2-Cyclohexyl-2-hydroxyphenylacetyl)oxy]-1,1-dimethyl-piperidinium bromide | — | 0.75 |
| Tartaric acid, sodium salt | 0.10 | 0.10 |
| Phenoxyethanol | 0.40 | 0.40 |
| Diazolidinylurea | 0.20 | 0.20 |
| Ethanol, denaturated | 8.00 | 8.00 |
| Ammoniumacryloyl dimethyltaurate/VP copolymer | 0.80 | 0.80 |
| Glycerin | 5.00 | 5.00 |
| Fillers, (distarch phosphate, BHT, talc) | 0.10 | 0.10 |
| Perfume, colorants | q.s. | q.s. |
| Water | ad 100 | ad 100 |

Example 19

Microemulsion

| Raw Material (INCI) | I | II |
|---|---|---|
| | % by weight | |
| Lecithin | 1.00 | 1.00 |
| Oleth-15 | 5.00 | 5.00 |
| Phenoxyethanol | 0.50 | 0.50 |
| Hexamidinylurea | 0.10 | 0.10 |
| Iodopropynylbutyl carbamate | 0.25 | 0.25 |
| Acrylates/$C_{10-30}$ alkyl acrylate crosspolymer | 0.30 | 0.30 |
| Polyurethane-4 (Avalure UR-445) | 0.50 | 0.50 |
| Hydrophobicized AMPS copolymer | 0.20 | 0.20 |
| 4-[(2-Cyclopentyl-2-hydroxyphenylacetyl)oxy]-1,1-dimethyl-piperidinium bromide | 1.00 | — |
| 4-[(2-Cyclohexyl-2-hydroxyphenylacetyl)oxy]-1,1-dimethyl-piperidinium bromide | — | 1.00 |
| Aluminum chlorohydrate | | |
| Glycerin | 6.00 | 6.00 |
| Perfume | q.s. | q.s. |
| Fillers (distarch phosphate, $SiO_2$, talc, aluminum stearate) | q.s. | q.s. |
| Water | ad 100 | ad 100 |

Example 20

Microemulsion

| Raw Material (INCI) | I | II |
|---|---|---|
| | % by weight | |
| Lecithin | 1.00 | 1.00 |
| Oleth-15 | 5.00 | 5.00 |

-continued

| Raw Material (INCI) | I | II |
|---|---|---|
| | % by weight | |
| Phenoxyethanol | 0.50 | 0.50 |
| Hexamidinylurea | 0.10 | 0.10 |
| Iodopropynylbutyl carbamate | 0.25 | 0.25 |
| Acrylates/C$_{10-30}$ alkyl acrylate crosspolymer | 0.30 | 0.30 |
| Polyurethane-4 (Avalure UR-445) | 0.50 | 0.50 |
| Hydrophobicized AMPS copolymer | 0.20 | 0.20 |
| 4-[(2-Cyclopentyl-2-hydroxyphenylacetyl)oxy]-1,1-dimethyl-piperidinium bromide | 1.00 | — |
| 4-[(2-Cyclohexyl-2-hydroxyphenylacetyl)oxy]-1,1-dimethyl-piperidinium bromide | — | 1.00 |
| Glycerin | 6.00 | 6.00 |
| Perfume | q.s. | q.s. |
| Fillers (distarch phosphate, SiO$_2$, talc, aluminum stearate) | q.s. | q.s. |
| Water | Ad 100 | Ad 100 |

Example 21

Transparent Microemulsion

Roll-On

| Raw Material (INCI) | I | II |
|---|---|---|
| | % by weight | |
| Glycerin monoisostearate | 1.00 | 1.00 |
| Polyoxyethylene(20)isostearyl ether | 2.00 | 2.00 |
| Di-n-octylcarbonate | 3.00 | 3.00 |
| 2-Octyldodecanol | 1.00 | 1.00 |
| Panthenol | 1.00 | 1.00 |
| Jojoba oil | 0.10 | 0.10 |
| Hydrophobically modified hydroxyethylcellulose | 0.20 | 0.20 |
| 4-[(2-Cyclopentyl-2-hydroxyphenylacetyl)oxy]-1,1-dimethyl-piperidinium bromide | 0.50 | — |
| 4-[(2-Cyclohexyl-2-hydroxyphenylacetyl)oxy]-1,1-dimethyl-piperidinium bromide | — | 0.50 |
| 2-Phenoxyethanol | 0.50 | 0.50 |
| Perfume, antioxidants | q.s. | q.s. |
| Water | ad 100 | ad 100 |

Example 22

Translucent Microemulsion

Atomizer

| Raw Material (INCI) | I | II |
|---|---|---|
| | % by weight | |
| Polyoxyethylene(20)cetylstearyl ether | 2.00 | 2.00 |
| Polyoxyethylene(12)cetylstearyl ether | 1.00 | 1.00 |
| Glycerin stearate | 2.00 | 2.00 |
| Cetylstearyl alcohol | 0.50 | 0.50 |
| Cetylpalmitate | 0.50 | 0.50 |
| Caprylic acid-capric acid ester | 3.00 | 3.00 |
| Di-n-octylether | 7.00 | 7.00 |
| Glycerin | 3.00 | 3.00 |
| Carrageenan | 0.2 | 0.2 |
| 4-[(2-Cyclopentyl-2-hydroxyphenylacetyl)oxy]-1,1-dimethyl-piperidinium bromide | 0.50 | — |

-continued

| Raw Material (INCI) | I | II |
|---|---|---|
| | % by weight | |
| 4-[(2-Cyclohexyl-2-hydroxyphenylacetyl)oxy]-1,1-dimethyl-piperidinium bromide | — | 0.50 |
| 2-Phenoxyethanol | 0.50 | 0.50 |
| Perfume, antioxidants | q.s. | q.s. |
| Water | ad 100 | ad 100 |

Example 23

Macroemulsion

Roll-On

| Raw Material (INCI) | I | II | III |
|---|---|---|---|
| | % by weight | | |
| Polyethyleneglycol(21)stearyl ether | 3.00 | 3.00 | 3.00 |
| Polyethyleneglycol(2)stearyl ether | 2.00 | 2.00 | 2.00 |
| Polypropyleneglycol(15)stearyl ether | 2.00 | 2.00 | 2.00 |
| EDTA | 0.1 | 0.1 | 0.1 |
| Acryloyldimethyl taurate | 0.4 | 0.4 | 0.4 |
| *Macadamia* oil | 0.10 | 0.10 | 0.10 |
| Perfume, antioxidants | q.s. | q.s. | q.s. |
| 2-Phenoxyethanol | 0.5 | 0.5 | 0.5 |
| 4-[(2-Cyclopentyl-2-hydroxyphenylacetyl)oxy]-1,1-dimethyl-piperidinium bromide | 1.50 | — | — |
| 4-[(2-Cyclohexyl-2-hydroxyphenylacetyl)oxy]-1,1-dimethyl-piperidinium bromide | — | 1.00 | — |
| 4-[(2-(2-Butyl)-2-hydroxyphenylacetyl)oxy]-1,1-dimethyl-piperidinium bromide | — | — | 1.00 |
| Water | ad 100 | ad 100 | ad 100 |

Example 24

Pump Atomizer

| Raw material (INCI) | I | II |
|---|---|---|
| | % by weight | |
| Ethanol | 55.00 | 55.00 |
| PEG-40 hydrogenated castor oil | 2.00 | 2.00 |
| Glycerin | 1.00 | 1.00 |
| 2-Butyloctanoic acid | 0.20 | 0.20 |
| 4-[(2-Cyclopentyl-2-hydroxyphenylacetyl)oxy]-1,1-dimethyl-piperidinium bromide | 0.50 | — |
| 4-[(2-Cyclohexyl-2-hydroxyphenylacetyl)oxy]-1,1-dimethyl-piperidinium bromide | — | 0.50 |
| Perfume | q.s. | q.s. |
| Water | ad 100.00 | ad 100.00 |

Example 25

Roll-On Gel

| Raw Material (INCI) | I | II % by weight | III |
|---|---|---|---|
| Ethanol | 50.00 | 50.00 | 50.00 |
| PEG-40 hydrogenated castor oil | 2.00 | 2.00 | 2.00 |
| Hydroxyethylcellulose | 0.50 | 0.50 | 0.50 |
| 2-Butyloctanoic acid | 0.20 | 0.30 | 0.30 |
| 4-[(2-Cyclopentyl-2-hydroxyphenylacetyl)oxy]-1,1-dimethyl-piperidinium bromide | 0.10 | 0.20 | — |
| 4-[(2-Cyclohexyl-2-hydroxyphenylacetyl)oxy]-1,1-dimethyl-piperidinium bromide | — | — | 0.20 |
| Aluminum chlorohydrate | — | 10.00 | 10.00 |
| Perfume | q.s. | q.s. | q.s. |
| Water | ad 100 | ad 100 | ad 100 |

Example 26

Roll-On Emulsion

| Raw Material (INCI) | I | II % by weight | III |
|---|---|---|---|
| Aluminum chlorohydrate | — | 10.00 | 10.00 |
| Polypropyleneglycol(15)stearyl ether | 5.00 | 5.00 | 5.00 |
| Polyethyleneglycol(100)stearyl ether | 1.00 | 1.00 | 1.00 |
| Polyethyleneglycol(2)stearyl ether | 4.00 | 4.00 | 4.00 |
| 2-Hexyldecanoic acid | 0.20 | 0.30 | 0.30 |
| 4-[(2-Cyclopentyl-2-hydroxyphenylacetyl)oxy]-1,1-dimethyl-piperidinium bromide | 1.00 | 3.00 | — |
| 4-[(2-Cyclohexyl-2-hydroxyphenylacetyl)oxy]-1,1-dimethyl-piperidinium bromide | — | — | 3.00 |
| Perfume, preservatives | q.s. | q.s. | q.s. |
| Water | ad 100.00 | ad 100.00 | ad 100.00 |

Example 27

Deodorant Stick Type A

| Raw material (INCI) | I | II % by weight | III |
|---|---|---|---|
| Sodium stearate | 7.00 | 7.00 | 7.00 |
| 1,2-Propyleneglycol | 48.00 | 48.00 | 48.00 |
| 4-[(2-Cyclopentyl-2-hydroxyphenylacetyl)oxy]-1,1-dimethyl-piperidinium bromide | 0.20 | 0.30 | — |
| 4-[(2-Cyclohexyl-2-hydroxyphenylacetyl)oxy]-1,1-dimethyl-piperidinium bromide | — | — | 0.30 |
| 2-Butyloctanoic acid | — | 0.10 | 0.10 |
| 2-Hexyldecanoic acid | 0.20 | — | — |
| Perfume, preservatives | q.s. | q.s. | q.s. |
| Water | ad 100 | ad 100 | ad 100 |

Example 28

Deodorant Stick Type B

| Raw Material (INCI) | I | II % by weight | III |
|---|---|---|---|
| Sodium stearate | 8.00 | 8.00 | 8.00 |
| 1,2-Propyleneglycol | 45.00 | 45.00 | 45.00 |
| 4-[(2-Cyclopentyl-2-hydroxyphenylacetyl)oxy]-1,1-dimethyl-piperidinium bromide | 0.20 | 0.30 | — |
| 4-[(2-Cyclohexyl-2-hydroxyphenylacetyl)oxy]-1,1-dimethyl-piperidinium bromide | — | — | 0.30 |
| 2-Butyloctanoic acid | — | 0.50 | 0.50 |
| 2-Hexyldecanoic acid | 0.50 | — | — |
| Polyethyleneglycol(25)cetearyl ether | 3.00 | 3.00 | 3.00 |
| Ethanol | 20.00 | 20.00 | 20.00 |
| Perfume, preservatives | q.s. | q.s. | q.s. |
| Water | ad 100 | ad 100 | ad 100 |

Example 29

Aerosol Spray

| | % by weight | | |
|---|---|---|---|
| Raw Material (INCI) | I | II | III |
| 4-[(2-Cyclopentyl-2-hydroxyphenylacetyl)oxy]-1,1-dimethyl-piperidinium bromide | 0.6 | 0.5 | — |
| 4-[(2-Cyclohexyl-2-hydroxyphenylacetyl)oxy]-1,1-dimethyl-piperidinium bromide | — | — | 0.50 |
| Chitosan lactate | 0.50 | 0.30 | — |
| Cyclomethicone | 8.50 | — | 12.80 |
| $C_{12-15}$ Alkyl benzoate | 3.00 | 5.00 | — |
| Dicaprylyl carbonate | — | 2.00 | — |
| Isohexadecane | — | 9.10 | — |
| Polydimethylsiloxane | 0.90 | 1.00 | 2.00 |
| Disteardimonium hectorite | 0.60 | — | 0.40 |
| Silicon dioxide | — | 1.10 | 0.30 |
| Talc | — | — | 3.00 |
| Perfume | 0.90 | 1.00 | 1.00 |
| Propellant gas mixture | 85.00 | 80.00 | 80.00 |
| Total | 100.00 | 100.00 | 100.00 |

Example 30

Stick

| | % by weight | | |
|---|---|---|---|
| Raw Material (INCI) | I | II | III |
| 4-[(2-Cyclopentyl-2-hydroxyphenylacetyl)oxy]-1,1-dimethyl-piperidinium bromide | 0.5 | 1.0 | — |
| 4-[(2-Cyclohexyl-2-hydroxyphenylacetyl)oxy]-1,1-dimethyl-piperidinium bromide | — | — | 0.5 |

-continued

| Raw Material (INCI) | % by weight | | |
|---|---|---|---|
| | I | II | III |
| Chitosan hydrochloride | 0.5 | 0.5 | — |
| Cyclomethicone | 51.0 | 45.0 | 45.2 |
| $C_{12-15}$ Alkyl benzoate | — | 15.0 | 10.0 |
| PPG-14 butyl ether | −15.0 | 5.0 | — |
| Polydimethylsiloxane | — | — | 10.0 |
| Disteardimonium hectorite | 1.0 | — | 1.0 |
| Silicon dioxide | — | 1.0 | 0.8 |
| Stearyl alcohol | 20.0 | 20.0 | 18.0 |
| Hydrogenated castor oil | 1.0 | 1.5 | 1.5 |
| Talc | 10.0 | 10.0 | 12.0 |
| Perfume | 1.0 | 1.0 | 1.0 |
| Total | 100.0 | 100.0 | 100.0 |

Example 31

Deodorant Roller

| Raw Material (INCI) | % by weight | | |
|---|---|---|---|
| | I | II | III |
| 4-[(2-Cyclopentyl-2-hydroxyphenylacetyl)oxy]-1,1-dimethyl-piperidinium bromide | 0.5 | 1.0 | — |
| 4-[(2-Cyclohexyl-2-hydroxyphenylacetyl)oxy]-1,1-dimethyl-piperidinium bromide | — | — | 1.0 |
| Chitosan acetate | 0.3 | 0.4 | 0.4 |
| Cyclomethicone | 82.2 | 76.0 | 76.0 |
| $C_{12-15}$ Alkyl benzoate | 2.0 | 5.0 | 5.0 |
| Polyisobutene | 0.5 | 2.0 | 2.0 |
| Isohexadecane | 10.0 | 5.0 | 5.0 |
| Quaternium-90 bentonite | 2.5 | 2.8 | 2.8 |
| Mineral oil | — | 5.0 | 5.0 |
| Propylene carbonate | 0.5 | 0.8 | 0.8 |
| Water | 0.5 | 1.0 | 1.0 |
| Perfume | 1.0 | 1.0 | 1.0 |
| Total | 100.0 | 100.0 | 100.0 |

Example 32

Transparent Microemulsion

Roll-On

| Raw Material (INCI) | I | II | III |
|---|---|---|---|
| | % by weight | | |
| Glycerin monoisostearate | 2.00 | 2.00 | 2.00 |
| Polyoxyethylene(20)isostearyl ether | 4.00 | 4.00 | 4.00 |
| Di-n-octyl carbonate | 2.00 | 2.00 | 2.00 |
| 2-Octyldodecanol | 2.00 | 2.00 | 2.00 |
| Glycerin | 3.00 | 3.00 | 3.00 |
| Avocado oil | 0.10 | 0.10 | 0.10 |
| 4-[(2-Cyclopentyl-2-hydroxyphenylacetyl)oxy]-1,1-dimethyl-piperidinium bromide | 0.05 | — | — |
| 4-[(2-Cyclohexyl-2-hydroxyphenylacetyl)oxy]-1,1-dimethyl-piperidinium bromide | — | 0.05 | — |
| 4-[(2-(2-Butyl)-2-hydroxyphenylacetyl)oxy]-1,1-dimethyl-piperidinium bromide | — | — | 0.05 |
| Chitosan | 0.50 | 0.50 | 0.50 |
| Lactic acid | 0.13 | 0.13 | 0.13 |
| Perfume, antioxidants | q.s. | q.s. | q.s. |
| Water | ad 100 | ad 100 | ad 100 |

Example 33

Translucent Microemulsion

Atomizer

| Raw Material (INCI) | I | II |
|---|---|---|
| | % by weight | |
| Polyoxyethylene(20)cetylstearyl ether | 3.00 | 3.00 |
| Polyoxyethylene(12)cetylstearyl ether | 0.50 | 0.50 |
| Glycerin stearate | 3.00 | 3.00 |
| Cetyl stearyl alcohol | 0.50 | 0.50 |
| Cetyl palmitate | 0.50 | 0.50 |
| Capryl/capric acid ester | 5.00 | 5.00 |
| Di-n-octylether | 5.00 | 5.00 |
| Glycerin | 4.00 | 4.00 |
| 4-[(2-Cyclopentyl-2-hydroxyphenylacetyl)oxy]-1,1-dimethyl-piperidinium bromide | 0.15 | — |
| 4-[(2-Cyclohexyl-2-hydroxyphenylacetyl)oxy]-1,1-dimethyl-piperidinium bromide | — | 0.15 |
| Chitosan lactate | 0.30 | 0.30 |
| Perfume, antioxidants | q.s. | q.s. |
| Water | ad 100 | ad 100 |

Example 34

Macroemulsion

Roll-On

| Raw Material (INCI) | I | II |
|---|---|---|
| | % by weight | |
| Polyethyleneglycol(21)stearyl ether | 2.00 | 2.00 |
| Polyethyleneglycol(2)stearyl ether | 2.50 | 2.50 |
| Polypropyleneglycol(15)stearyl ether | 3.00 | 3.00 |
| Trisodium salt of ethylenediaminetetraacetic acid (20% aqueous solution) | 1.50 | 1.50 |
| Avocado oil | 0.10 | 0.10 |
| Perfume, antioxidants | q.s. | q.s. |
| Lactic acid | 0.1 | 0.1 |
| Chitosan | 0.5 | 0.5 |
| 4-[(2-Cyclopentyl-2-hydroxyphenylacetyl)oxy]-1,1-dimethyl-piperidinium bromide | 0.25 | — |
| 4-[(2-Cyclohexyl-2-hydroxyphenylacetyl)oxy]-1,1-dimethyl-piperidinium bromide | — | 0.25 |
| Water | ad 100 | ad 100 |

Example 35

Alcoholic Solution

Roll-On

| Raw Material (INCI) | I | II |
|---|---|---|
| | % by weight | |
| Alcohol denat. | 20.00 | 20.00 |
| Hydroxyethylcellulose | 0.40 | 0.40 |
| Polyethyleneglycol 400 | 3.00 | 3.00 |
| Polyethyleneglycol (2000) hydrogenated castor oil | 2.00 | 2.00 |
| Avocado oil | 0.50 | 0.50 |
| 4-[(2-Cyclopentyl-2-hydroxyphenylacetyl)oxy]-1,1-dimethyl-piperidinium bromide | 0.05 | — |
| 4-[(2-Cyclohexyl-2-hydroxyphenylacetyl)oxy]-1,1-dimethyl-piperidinium bromide | — | 0.05 |
| Chitosan hydrochloride | 0.2 | 0.2 |
| Perfume, antioxidants | q.s. | q.s. |
| Water | ad 100 | ad 100 |

Example 36

O/W Gel Cream

| Raw Material (INCI) | I | II |
|---|---|---|
| | % by weight | |
| Glyceryl stearate citrate | 1.25 | 1.25 |
| Cetylstearyl alcohol | 0.75 | 0.75 |
| Caprylic/capric triglyceride | 1.00 | 1.00 |
| Dicapryl carbonate | 2.00 | 2.00 |
| Dimethylpolysiloxane, cyclic (dimethicone) | 4.00 | 4.00 |
| Carbopol | 0.15 | 0.15 |
| Acrylic acid/C10-30 alkylmethacrylate-copolymer | 0.25 | 0.25 |
| Dimethicone | 0.75 | 0.75 |
| Jojoba oil | 1.00 | 1.00 |
| Myristyl myristate | 1.00 | 1.00 |
| Tocopheryl acetate | 0.75 | 0.75 |
| Glycerin | 10.00 | 10.00 |
| Ethanol | 1.00 | 1.00 |
| Chitosan lactate | 0.80 | 0.80 |
| 4-[(2-Cyclopentyl-2-hydroxyphenylacetyl)oxy]-1,1-dimethyl-piperidinium bromide | 1.50 | — |
| 4-[(2-Cyclohexyl-2-hydroxyphenylacetyl)oxy]-1,1-dimethyl-piperidinium bromide | — | 1.50 |
| Perfume | q.s. | q.s. |
| Preservatives | q.s. | q.s. |
| Water | ad 100 | ad 100 | pH value adjusted to 5.0

Example 37

O/W Emulsion

| Raw Material (INCI) | I | II |
|---|---|---|
| | % by weight | |
| Glyceryl stearate citrate | 3.00 | 3.00 |
| Stearyl alcohol | 1.00 | 1.00 |
| Caprylic/capric triglyceride | 1.00 | 1.00 |
| Octyldodecanol | 1.00 | 1.00 |
| Dicapryl ether | 1.00 | 1.00 |
| Lactic acid | 0.08 | 0.08 |
| Chitosan | 0.30 | 0.30 |
| 4-[(2-Cyclopentyl-2-hydroxyphenylacetyl)oxy]-1,1-dimethyl-piperidinium bromide | 0.50 | — |
| 4-[(2-Cyclohexyl-2-hydroxyphenylacetyl)oxy]-1,1-dimethyl-piperidinium bromide | — | 0.50 |
| Carbomer | 0.15 | 0.15 |
| Glycerin | 3.00 | 3.00 |
| Perfume, preservatives, colorants, antioxidants, etc. | q.s. | q.s. |
| Water | Ad 100 | Ad 100 | pH value adjusted to 5.5

Example 38

O/W Emulsion

| Raw Material (INCI) | I | II |
|---|---|---|
| | % by weight | |
| Polyglyceryl-3-methyl glucose distearate | 3.00 | 3.00 |
| Stearyl alcohol | 3.00 | 3.00 |
| C$_{12-15}$ Alkyl benzoate | 3.00 | 3.00 |
| Butylene glycol dicaprylate/dicaprate | 2.00 | 2.00 |
| Caprylic acid/capric acid triglyceride | 3.00 | 3.00 |
| Hydrogenated polydecene | 2.00 | 2.00 |
| Dimethylpolysiloxane (dimethicone) | 1.00 | 1.00 |
| Lactic acid | 0.25 | 0.25 |
| Chitosan | 1.00 | 1.00 |
| 4-[(2-Cyclopentyl-2-hydroxyphenylacetyl)oxy]-1,1-dimethyl-piperidinium bromide | 2.00 | — |
| 4-[(2-Cyclohexyl-2-hydroxyphenylacetyl)oxy]-1,1-dimethyl-piperidinium bromide | — | 2.00 |
| Sodium ascorbyl phosphate | 0.10 | 0.10 |
| Phenoxyethanol | 0.40 | 0.40 |
| Iodopropynylbutyl carbamate | 0.05 | 0.05 |
| p-Hydroxybenzoic alkyl ester (paraben) | 0.20 | 0.20 |
| Xanthan gum | 0.10 | 0.10 |
| Carbomer | 0.10 | 0.10 |
| Butylene glycol | 2.00 | 2.00 |
| Additives (talc, BHT) | 0.50 | 0.50 |
| Perfume | q.s. | q.s. |
| Water | ad 100 | ad 100 |

Example 39

O/W Emulsion

| Raw Material (INCI) | I | II |
|---|---|---|
| | % by weight | |
| PEG-40 stearate | 2.00 | 2.00 |
| Glyceryl stearate | 2.00 | 2.00 |
| Stearyl alcohol | 0.50 | 0.50 |
| Cetyl alcohol | 2.00 | 2.00 |
| C$_{12-15}$ Alkyl benzoate | 2.00 | 2.00 |
| Caprylic acid/capric acid triglyceride | 1.00 | 1.00 |
| Cyclomethicone | 3.00 | 3.00 |
| Cicaprylyl carbonate | 2.00 | 2.00 |
| Lactic acid | 0.25 | 0.25 |
| Chitosan | 1.00 | 1.00 |
| 4-[(2-Cyclopentyl-2-hydroxyphenylacetyl)oxy]-1,1-dimethyl-piperidinium bromide | 0.75 | — |

-continued

| Raw Material (INCI) | I | II |
|---|---|---|
| | % by weight | |
| 4-[(2-Cyclohexyl-2-hydroxyphenylacetyl)oxy]-1,1-dimethyl-piperidinium bromide | — | 0.75 |
| Tartaric acid, sodium salt | 0.10 | 0.10 |
| Phenoxyethanol | 0.40 | 0.40 |
| Diazolidinylurea | 0.20 | 0.20 |
| Ethanol denaturated | 8.00 | 8.00 |
| Ammonium acryloyldimethyltaurate/VP copolymer | 0.80 | 0.80 |
| Glycerin | 5.00 | 5.00 |
| Fillers (distarch phosphate, $SiO_2$, talc, aluminum stearate) | 0.10 | 0.10 |
| Perfume, colorants | q.s | q.s |
| Water | ad 100 | ad 100 |

Example 41

Microemulsion

| Raw Material (INCI) | I | II |
|---|---|---|
| | % by weight | |
| Lecithin | 1.00 | 1.00 |
| Oleth-15 | 5.00 | 5.00 |
| Phenoxyethanol | 0.50 | 0.50 |
| Hexamidinylurea | 0.10 | 0.10 |
| Iodopropynyl butylcarbamate | 0.25 | 0.25 |
| Xanthan gum | 0.10 | 0.10 |
| Polyurethane-4(Avalure UR-445) | 0.50 | 0.50 |
| Hydrophobicized AMPS copolymer | 0.20 | 0.20 |
| Chitosan | 0.30 | 0.30 |
| Lactic acid | 0.08 | 0.08 |
| 4-[(2-Cyclopentyl-2-hydroxyphenylacetyl)oxy]-1,1-dimethyl-piperidinium bromide | 1.00 | — |
| 4-[(2-Cyclohexyl-2-hydroxyphenylacetyl)oxy]-1,1-dimethyl-piperidinium bromide | — | 1.00 |
| Glycerin | 6.00 | 6.00 |
| Perfume | q.s. | q.s. |
| Fillers (distarch phosphate, $SiO_2$, talc, aluminum stearate) | q.s. | q.s. |
| Water | ad 100 | ad 100 |

Example 41

Aerosol Spray

| Raw Material (INCI) | I | II | III |
|---|---|---|---|
| | % by weight | | |
| 4-[(2-Cyclopentyl-2-hydroxyphenylacetyl)oxy]-1,1-dimethyl-piperidinium bromide | — | 0.5 | 0.5 |
| 4-[(2-Cyclohexyl-2-hydroxyphenylacetyl)oxy]-1,1-dimethyl-piperidinium bromide | 0.50 | | |
| Cyclomethicone | 9.0 | — | 12.8 |
| $C_{12}$-$C_{15}$ Alkyl benzoate | 3.0 | 5.0 | — |
| Dicaprylyl carbonate | — | 2.0 | — |
| Isohexadecane | — | 9.4 | — |
| Polydimethylsiloxane | 0.9 | 1.0 | 2.0 |
| Disteardimonium hectorite | 0.6 | — | 0.4 |
| Silicon dioxide | — | 1.1 | 0.3 |
| Talc | — | — | 3.0 |
| Perfume | 0.9 | 1.0 | 1.0 |
| Propellant gas mixture | 85.0 | 80.0 | 80.0 |
| Total | 100.0 | 100.0 | 100.0 |

Example 42

Sticks

| Raw Material (INCI) | I | II | III |
|---|---|---|---|
| | % by weight | | |
| 4-[(2-Cyclopentyl-2-hydroxyphenylacetyl)oxy]-1,1-dimethyl-piperidinium bromide | 0.5 | 1.0 | 0.5 |
| 4-[(2-Cyclohexyl-2-hydroxyphenylacetyl)oxy]-1,1-dimethyl-piperidinium bromide | 0.5 | 1.0 | — |
| Cyclomethicone | 51.5 | 45.5 | 45.5 |
| $C_{12}$-$_{15}$ Alkyl benzoate | — | 15.0 | 10.0 |
| PPG-14 butyl ether | 15.0 | 5.0 | — |
| Polydimethylsiloxane | — | — | 10.0 |
| Disteardimonium hectorite | 1.0 | — | 1.0 |
| Silicon dioxide | — | 1.0 | 0.5 |
| Stearyl alcohol | 20.0 | 20.0 | 18.0 |
| Hydrogenated castor oil | 1.0 | 1.5 | 1.5 |
| Talc | 10.0 | 10.0 | 12.0 |
| Perfume | 1.0 | 1.0 | 1.0 |
| Total | 100.0 | 100.0 | 100.0 |

Example 43

Deodorant Rollers

| Raw Material (INCI) | I | II | III |
|---|---|---|---|
| | % by weight | | |
| 4-[(2-Cyclopentyl-2-hydroxyphenylacetyl)oxy]-1,1-dimethyl-piperidinium bromide | 0.5 | 1.0 | — |
| 4-[(2-Cyclohexyl-2-hydroxyphenylacetyl)oxy]-1,1-dimethyl-piperidinium bromide | — | — | 1.0 |
| Cyclomethicone | 82.5 | 76.4 | 76.4 |
| $C_{12}$-$_{15}$ Alkyl benzoate | 2.0 | 5.0 | 5.0 |
| Polyisobutene | 0.5 | 2.0 | 2.0 |
| Isohexadecane | 10.0 | 5.0 | 5.0 |
| Quaternium-90 bentonite | 2.5 | 2.8 | 2.8 |
| Mineral oil | — | 5.0 | 5.0 |
| Propylene carbonate | 0.5 | 0.8 | 0.8 |
| Water | 0.5 | 1.0 | 1.0 |
| Perfume | 1.0 | 1.0 | 1.0 |
| Total | 100.0 | 100.0 | 100.0 |

Example 44

Skin Cleansing Gels

| Raw Material (INCI) | % by weight | | | | |
|---|---|---|---|---|---|
| | I | II | III | IV | V |
| Sodium laureth sulfate | 13.2 | 11 | 9.5 | 11 | 9.5 |
| Cocamidopropyl betaine | 1.65 | 3.3 | 3.8 | 3.3 | 3.8 |
| PEG-7 glyceryl cocoate | — | — | — | 2.0 | 2.0 |
| Laureth-2 | — | — | — | 0.1 | — |
| PEG-90 glyceryl isosterate | — | — | — | 0.3 | — |
| Sodium cocoyl glutamate | 1.25 | 0.75 | 2.5 | 0.75 | 0.75 |
| PEG-40 hydrogenated castor oil | 0.50 | 0.50 | 0.50 | 0.50 | 0.50 |
| PEG-100 hydrogenated glyceryl palmitate | 0.50 | 0.50 | 0.50 | 0.50 | 0.50 |
| 4-[(2-Cyclopentyl-2-hydroxyphenyl-acetyl)oxy]-1,1-dimethyl-piperidinium bromide | 0.025 | 0.025 | 0.05 | 0.02 | 0.1 |
| Polyquaternium-10 | 0.2 | — | 0.20 | — | — |
| Sodium benzoate | 0.45 | 0.45 | 0.45 | 0.45 | 0.45 |
| Sodium salicylate | 0.20 | 0.20 | 0.20 | 0.20 | 0.20 |
| Citric acid | 0.50 | 0.50 | 0.5 | 0.50 | 0.50 |
| Perfume | q.s. | q.s. | q.s. | q.s. | q.s. |
| Water | ad 100 | ad 100 | ad 100 | ad 100 | ad 100 |

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A cosmetic or dermatological composition, wherein the composition comprises from 0.05% to 15% by weight, based on a total weight of the composition, of at least one piperidinium salt of formula (I):

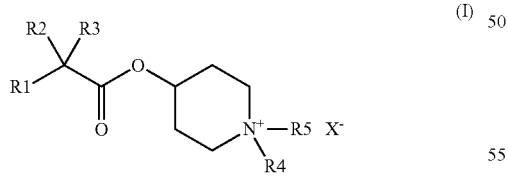

(I)

wherein:
$R_4$ and $R_5$ independently represent H or $C_1$-$C_6$ alkyl;
$R_4$ represents optionally substituted phenyl;
$R_3$ represents optionally substituted $C_3$-$C_8$ cycloalkyl or optionally substituted $C_1$-$C_6$ alkyl;
$R_2$ represents H, OH and OR wherein R represents $C_1$-$C_7$ alkyl; and
$X^-$ represents a cosmetically or dermatologically acceptable anion;
in a cosmetically or dermatologically acceptable carrier that comprises at least one of a deodorizing substance, a perfume, a pigment, an emollient, a moisturizer, a humectant, an anti-inflammatory substance, a light protection agent, an insect repellent, a bactericide, a virucide, an antimicrobial, a proteolytic substance, a keratolytic substance, and a foam stabilizer.

2. The composition of claim 1, wherein in formula (I)
$R_4$ and $R_5$ independently represent $C_1$-$C_4$ alkyl;
$R_3$ represents optionally substituted $C_3$-$C_8$ cycloalkyl or optionally substituted isopropyl, 2-butyl, 2-pentyl, 3-pentyl, 2-hexyl or 3-hexyl; and
$R_2$ represents H, OH or OR, wherein R represents $C_1$-$C_3$ alkyl.

3. The composition of claim 2, wherein in formula (I)
$R_4$ and $R_5$ independently represent $C_1$-$C_3$ alkyl;
$R_3$ represents isopropyl, 2-butyl, 2-pentyl, 3-pentyl, 2-hexyl, 3-hexyl or optionally substituted $C_3$-$C_8$ cycloalkyl.

4. The composition of claim 3, wherein in formula (I)
$R_4$ and $R_5$ are identical and represent methyl or ethyl;
$R_1$ represents unsubstituted phenyl;
$R_3$ represents 2-butyl or optionally substituted $C_4$-$C_6$ cycloalkyl; and
$R_2$ represents H or OH.

5. The composition of claim 4, wherein in formula (I)
$R_4$ and $R_5$ represent methyl; and
$R_3$ represents 2-butyl, optionally substituted cyclopentyl or optionally substituted cyclohexyl.

6. The composition of claim 5, wherein in formula (I)
$R_3$ represents 2-butyl, cyclopentyl and cyclohexyl.

7. The composition of claim 1, wherein X represents halogen, sulfate, carbonate, ascorbate or phosphate.

8. The composition of claim 1, wherein X represents halogen.

9. The composition of claim 1, wherein the composition comprises at least one of
(a) a 4-[(2-cyclopentyl-2-hydroxyphenylacetyl)oxy]-1,1-dimethyl-piperidinium salt of formula

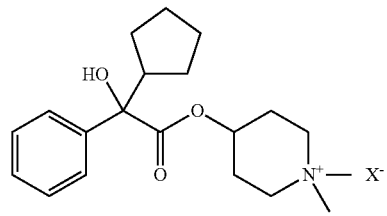

(b) a 4-{[2-(2-butyl)-phenylacetyl]oxy}-1,1-dimethyl-piperidinium salt of formula

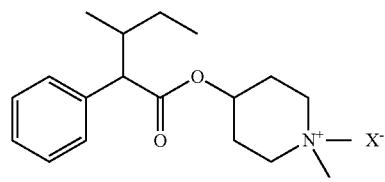

and
(c) a 4-[(2-cyclohexyl-2-hydroxyphenylacetyl)oxy]-1,1-dimethyl-piperidinium salt of formula

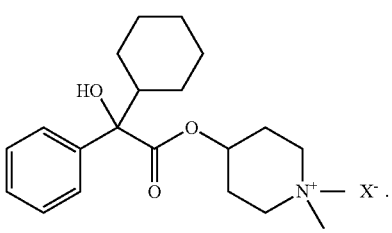

10. The composition of claim 9, wherein X represents halogen, sulfate, carbonate, ascorbate or phosphate.

11. The composition of claim 9, wherein X is Cl, Br or I.

12. The composition of claim 9, wherein X represents Br.

13. The composition of claim 1, wherein the at least one salt of formula (I) is present in a concentration of from about 0.1% to about 10% by weight.

14. The composition of claim 1, wherein the composition further comprises at least one deodorizing substance.

15. The composition of claim 1, wherein the composition is present as at least one of a cream, a lotion, a gel, an ointment, a tincture, a skin oil, a milk, a balm, an impregnated cloth, textile or pad, a roll-on, and a stick.

16. The composition of claim 1, wherein the composition is substantially free of aluminum compounds.

17. A method for reducing or inhibiting perspiration, wherein the method comprises applying an antiperspirant-effective amount of the composition of claim 1 to skin.

18. The method of claim 17, wherein the composition is applied by using ultrasound, an iontophoresis apparatus, a microchannel or a microneedle.

19. The composition of claim 1, wherein the composition comprises 4-[(2-cyclopentyl-2-hydroxyphenylacetyl)oxy]-1,1-dimethyl-piperidinium bromide of formula:

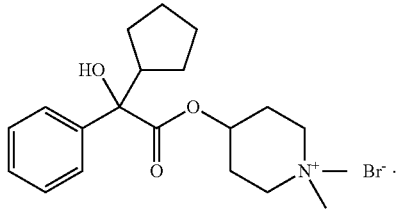 [SMILES: C[N+]1(C)CCC(OC(=O)C(O)(c2ccccc2)C2CCCC2)CC1 ; [Br-]]

20. A method for reducing or inhibiting perspiration, wherein the method comprises applying an antiperspirant-effective amount of the composition of 19 to skin.

21. The composition of claim 1, wherein the composition comprises 4-[(2-cyclohexyl-2-hydroxyphenylacetyl)oxy]-1,1-dimethyl-piperidinium bromide of formula:

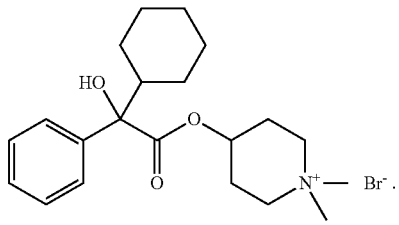 [SMILES: C[N+]1(C)CCC(OC(=O)C(O)(c2ccccc2)C2CCCCC2)CC1 ; [Br-]]

22. A method for reducing or inhibiting perspiration, wherein the method comprises applying an antiperspirant-effective amount of the composition of claim 21 to skin.

23. The composition of claim 1, wherein the composition comprises a compound of formula:

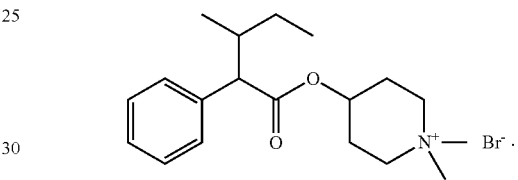

24. A method for reducing or inhibiting perspiration, wherein the method comprises applying an antiperspirant-effective amount of the composition of claim 23 to skin.

* * * * *